United States Patent [19]

Queener et al.

[11] Patent Number: 5,658,755

[45] Date of Patent: *Aug. 19, 1997

[54] METHOD FOR EXTRA-CELLULAR EXPRESSION OF PROTEIN

[75] Inventors: Stephen W. Queener, Indianapolis; Joseph M. Zock, Greenwood, both of Ind.

[73] Assignee: Eli Lilly and Company, Indianapolis, Ind.

[ * ] Notice: The term of this patent shall not extend beyond the expiration date of Pat. No. 5,451,522.

[21] Appl. No.: 275,487

[22] Filed: Jul. 15, 1994

[51] Int. Cl.$^6$ .............. C12P 21/00; C12N 9/64; C12N 9/80; C12N 9/86

[52] U.S. Cl. ............ 435/69.1; 435/69.4; 435/69.51; 435/69.52; 435/69.6; 435/69.8; 435/226; 435/228; 435/231

[58] Field of Search ................. 435/69.1, 69.4, 435/69.51, 69.8, 69.52, 69.6, 228, 231, 226

[56] References Cited

U.S. PATENT DOCUMENTS

| | | | |
|---|---|---|---|
| 4,977,089 | 12/1990 | Kovacevic et al. | 435/252.31 |
| 5,032,510 | 7/1991 | Kovacevic et al. | 435/69.1 |
| 5,200,327 | 4/1993 | Garvin et al. | 435/69.5 |
| 5,451,522 | 9/1995 | Queener et al. | 435/252.3 |

OTHER PUBLICATIONS

Kuhstoss et al. (1991), Gene 103:97–99.

Smith, Gale E., et al., *Molecular and Cellular Biology*, vol. 3, No. 12, pp. 2156–2165, Dec. 1983.

*Primary Examiner*—Mindy Fleisher
*Assistant Examiner*—Nancy J. Degen
*Attorney, Agent, or Firm*—Thomas D. Webster; Paul R. Cantrell; David E. Boone

[57] ABSTRACT

Heterologous extra-cellular expression of recombinant proteins in soluble functional form is desirable because of the ease associated with purification of the secreted proteins and avoidance of the need for cell extraction and protein refolding procedures. The present invention provides DNA sequences of the naturally-occurring phthalyl amidase gene isolated from *Xanthobacter agilis* that control transcription, translation, and extra-cellular secretion of proteins in *Streptomyces lividans*. These DNA sequences can be used in a method for extra-cellular expression of a wide variety of proteins in soluble functional form.

12 Claims, 3 Drawing Sheets

Function and restriction map of plasmid vector pZPA600.
Abbreviations: PAorf = phthalyl amidase open reading frame. tsr = gene enabling resistance to thiostrepton.

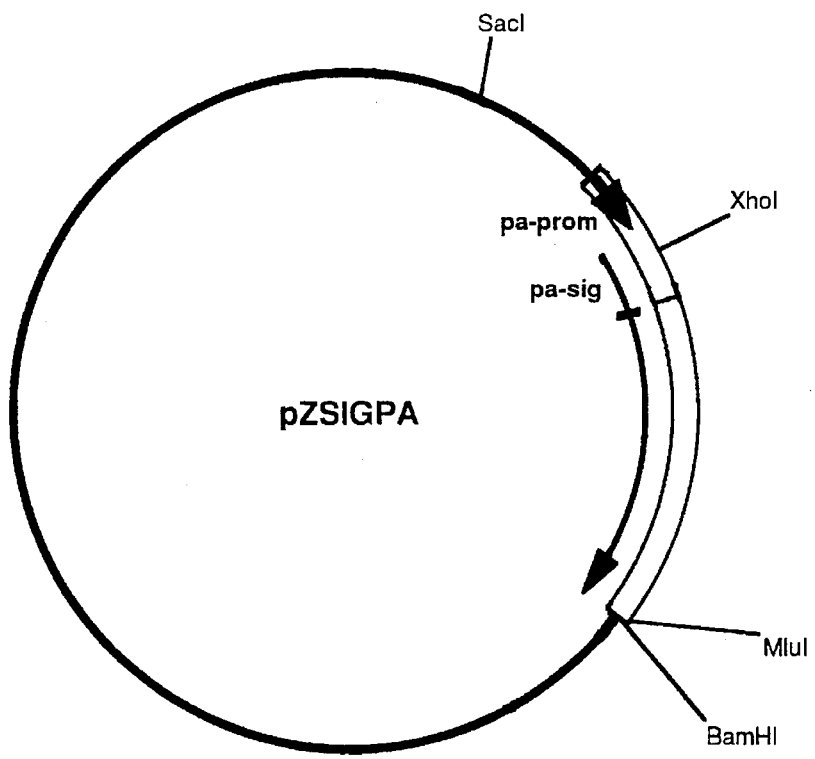

Figure 2. Map of functional elements and restriction enzyme sites for plasmid pZSIGPA. Pa-prom (short arrow) is the promoter sequence of the *Xanthobacter agilis* phthalyl amidase gene. The long arrow represents a portion of the phthalyl amidase ORF. Pa-sig (part of the long arrow) is the sequence encoding the signal peptide. The open box represents *Xanthobacter agilis* DNA.

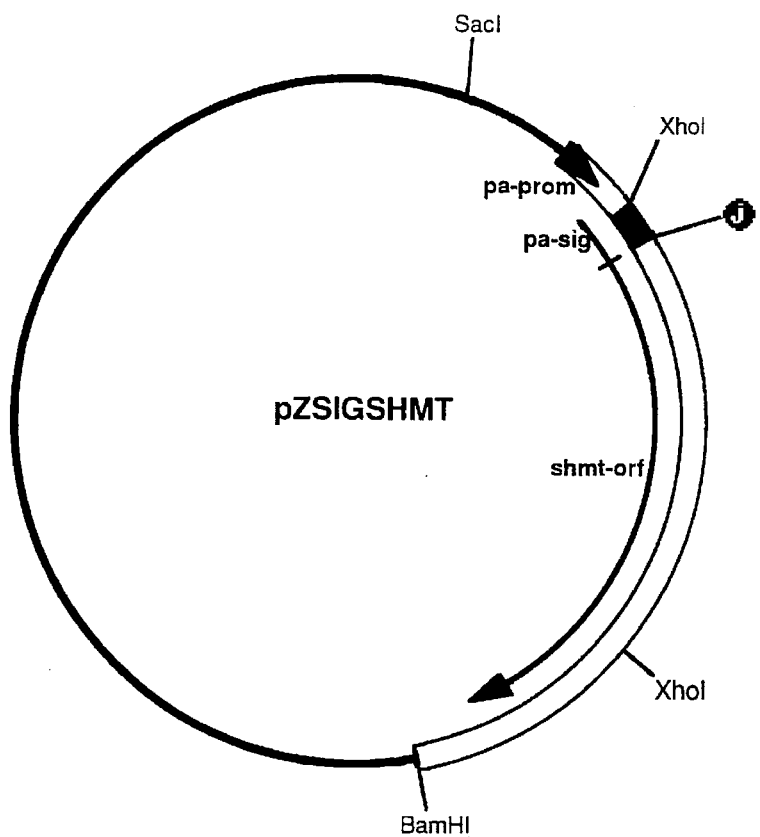

Figure 3. Map of functional elements and enzyme restriction sites for plasmid pZSIGSHMT. Pa-prom and Pa-sig as in Figure 2. Shmt-orf is a sequence encoding that portion of the fusion protein comprising the serine hydroxymethyl transferase polypeptide. Black box is the linker sequence described in Example 3. The (j) marks the junction formed by ligation of the linker sequence to the NdeI-BamHI fragment containing the shmt-orf as described in Example 6.

METHOD FOR EXTRA-CELLULAR EXPRESSION OF PROTEIN

BACKGROUND OF THE INVENTION

The present invention relates to the discovery that the regulatory control elements of the phthalyl amidase gene isolated from *Xanthobacter agilis* may be used to drive extra-cellular expression of desired proteins in a heterologous host.

Heterologous expression of recombinant proteins generally results in production of non-soluble material that must be extracted from the transformed cell, solubilized with denaturant, and refolded into the proper configuration in order to obtain soluble functional protein. Thus, a method for extra-cellular expression of soluble proteins is desirable because of the ease associated with purification of the secreted proteins and avoidance of the need for cell extraction and protein refolding procedures.

SUMMARY OF THE INVENTION

The present invention provides for DNA sequences of the naturally-occurring phthalyl amidase gene isolated from *Xanthobacter agilis* that control transcription, translation, and extra-cellular secretion of proteins in a heterologous host.

Thus, the present invention provides a method for expressing a protein, said method comprising:
a) positioning a nucleotide sequence encoding said protein in a DNA vector adjacent to and downstream from a signal peptide-encoding nucleotide sequence functional in *Streptomyces lividans*;
b) transforming a host cell with said vector; and
c) culturing said host cell under conditions suitable for gene expression, whereby said protein is secreted in soluble form.

Preferred DNA sequences for use in the DNA vector and resulting in extra-cellular production of protein include the promoter-bearing region (SEQ ID NO:7), the signal peptide-encoding sequence (SEQ ID NO:8), and the 3'-untranslated region (SEQ ID NO:10), all isolated from the phthalyl amidase gene residing in *Xanthobacter agilis*.

Preferred host cells are of the genus Streptomyces. The species *Streptomyces lividans* is especially preferred.

Definitions:

Coding sequence—the sequence of DNA in the open reading frame (ORF) of a gene that encodes the amino acid residue sequence of the protein expressed from the gene.

Gene—a segment of DNA that comprises a promoter, translational activating sequence, coding sequence, and 3' regulatory sequences, positioned to drive expression of the gene product.

Promoter—a DNA sequence that directs or initiates the transcription of DNA.

Recombinant DNA vector—any autonomously replicating or integrating DNA agent, including but not limited to plasmids, comprising a promoter and other regulatory sequences positioned to drive expression of a DNA sequence that encodes a polypeptide or RNA.

Recombinant DNA sequence—any DNA sequence, excluding the host chromosome from which the DNA is derived, which comprises a DNA sequence that has been isolated, synthesized, or partially synthesized.

Restriction fragment—any linear DNA molecule generated by the action of one or more restriction enzymes.

Translation activating sequence—a regulatory DNA sequence that, when transcribed into mRNA, promotes translation of mRNA into protein.

Signal peptide—a clearable amino acid sequence appearing at the amino-terminus of a proprotein which promotes transmembrane migration and extra-cellular production of the mature protein.

All nucleotide and amino acid abbreviations used in this disclosure are those accepted by the United States Patent and Trademark Office as set forth in 37 C.F.R. §1.822(b) (1993).

BRIEF DESCRIPTION OF THE FIGURES

The restriction enzyme and function maps presented in the drawings are approximate representations of the recombinant DNA vectors discussed herein. The restriction site information is not exhaustive. There may be more restriction enzymes sites of a given type than are actually shown on the map.

FIG. 2 is a restriction enzyme site and function map of plasmid pZSIGPA.

FIG. 3 is a restriction enzyme site and function map of plasmid pZSIGSHMT.

DETAILED DESCRIPTION OF THE INVENTION

Figure 1:
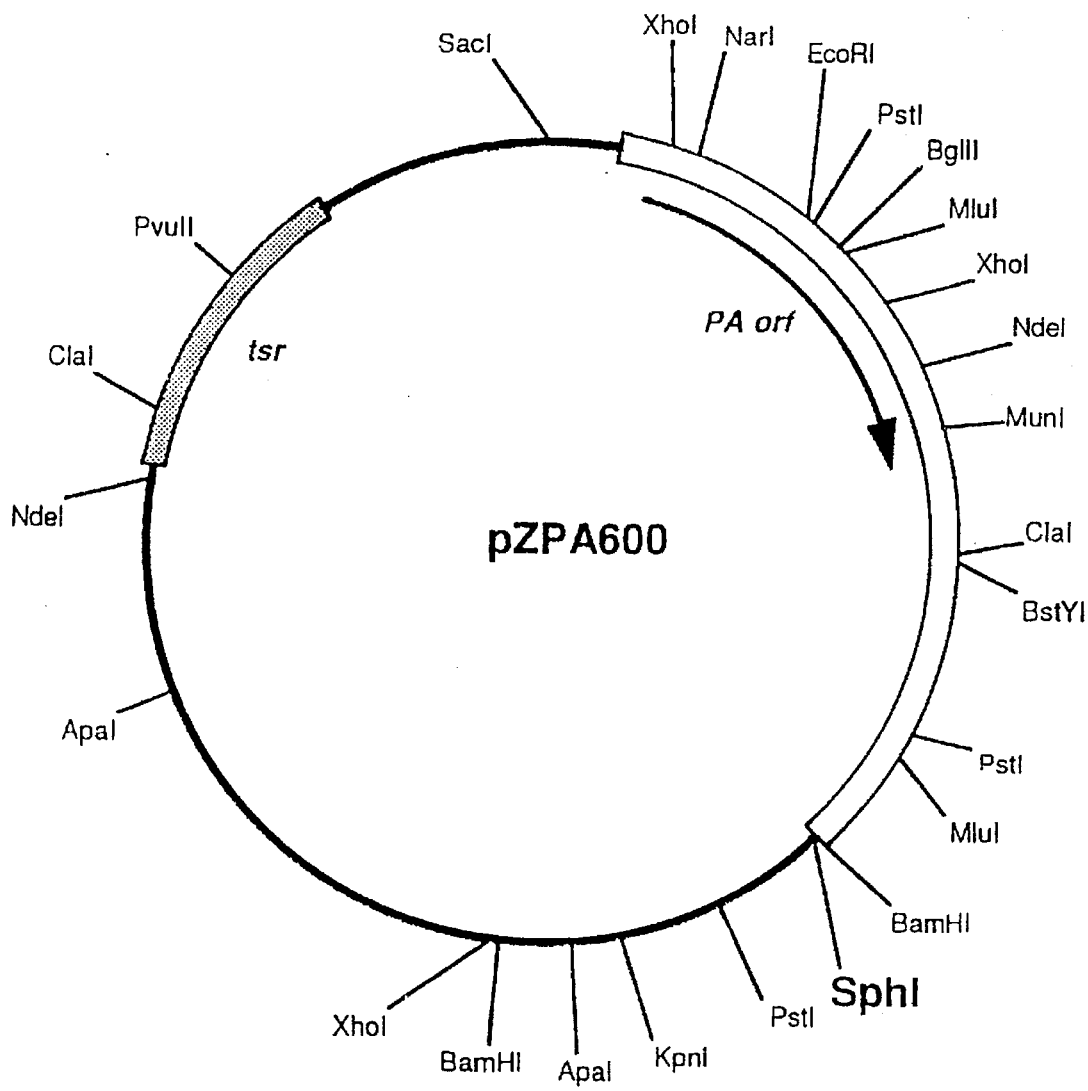
FIG. 1 is a restriction enzyme site and function map of plasmid pZPA600.

U.S. Pat No. 5,451,522, issued Sep. 19, 1995 is herein incorporated by reference.

Recombinant amino acid sequences, including proteins, enzymes, peptides, and peptide hormones (collectively referred to herein as proteins), may be produced by cloning DNA encoding the desired protein into a variety of vectors by means that are well known in the art. A number of suitable vectors may be used, including cosmids, plasmids, bacteriophage, and viruses. One of the principle requirements for such a vector is that it be capable of reproducing itself and transforming a host cell. Typical expression vectors comprise a promoter region, a 5'-untranslated region, a coding sequence, a 3'-untranslated region, an origin of replication, a selective marker, and a transcription termination site.

The current invention provides DNA sequences that control transcription, translation, and extra-cellular secretion of proteins in *Streptomyces lividans*, recombinant DNA vectors utilizing said DNA sequences, host cells transformed with said DNA vectors, and a method for expressing recombinant proteins in extra-cellular, soluble, functional form.

The method makes use of the DNA regulatory sequences of the phthalyl amidase gene (SEQ ID NO:6) originally isolated from *Xanthobacter agilis*, namely, SEQ ID NO:7; SEQ ID NO:8; and SEQ ID NO:10. These sequences, when transformed into *Streptomyces lividans* as part of a self-replicating vector, enable the host to produce and secrete soluble, properly-folded, functional proteins in an amount in excess of the amount of a cell-bound form produced by the natural source of the protein.

SEQ ID NO:7, which includes the promoter-bearing nucleotides 1–135 of SEQ ID NO:6, promotes transcription of the signal peptide and mature protein-encoding sequences. SEQ ID NO:8 (nucleotides 136–261 of SEQ ID NO:6) encodes the signal peptide portion of the coding sequence (SEQ ID NO:4). The signal peptide (SEQ ID NO:9), which provides for transport of the protein across the microbial cell wall of *Streptomyces lividans*, is cleaved from the protein by the cell, thereby enabling extra-cellular production of the mature protein. SEQ ID NO:10 (nucleotides 1621–3029 of SEQ ID NO:6) is a 3'-untranslated region which assists proper and efficient translation termination of the mRNA that encodes the protein. Those skilled in the art will recognize that the promoter of SEQ ID NO:7 and the 3'-untranslated region of SEQ ID NO:10 are not critical to expression of proteins in soluble form and can be substituted, respectively, for by other known promoters and translation termination regulatory sequences.

Thus, all that is needed to practice the current invention is that a DNA sequence encoding a signal peptide functional in *Streptomyces lividans*, preferably SEQ ID NO:8, be placed adjacent to and upstream from the ORF encoding the protein to be expressed and that this ORF be placed into a DNA vector used to transform the host cell, particularly *Streptomyces lividans*.

Use of the specific *Xanthobacter agilis* promoter (SEQ ID NO:7), placed adjacent to and upstream from the signal peptide is also preferred. Moreover, use of the 3'-untranslated region of SEQ IS NO:10 placed adjacent to and downstream from the protein to be expressed is preferred.

Thus, in a preferred embodiment of the invention, a DNA compound, which encodes the desired protein and which includes the transcriptional and translational regulatory elements of the phthalyl amidase gene isolated from the bacterium *Xanthobacter agilis* is used to transform *Streptomyces lividans*.

In particular, the DNA sequence encoding mature phthalyl amidase (SEQ ID NO:1), which corresponds to nucleotides 262–1620 of SEQ ID NO:6, may be replaced in SEQ ID NO:6 by a heterologous ORF from a wide variety of organisms wherein the heterologous ORF encodes a mature protein and introns are absent from those ORFs, either by nature or by virtue of precise removal from genomic DNA to form cDNA ORFs. In this arrangement, the regulatory elements of the phthalyl amidase gene continue to function such that the substituted DNA sequences are expressed and the proteins encoded thereby are produced and secreted from Streptomyces transformed with the modified DNA sequences. Thus, substitution of a desired protein-encoding sequence for the coding sequence of mature phthalyl amidase enables economic extra-cellular production of numerous proteins.

This method is particularly useful when the protein to be expressed is known to be secreted by its natural host or another surrogate host. This often occurs when the protein to be expressed is encoded by a DNA compound that includes a signal peptide-encoding nucleotide sequence positioned immediately adjacent to the 5'-terminal end (i.e., upstream) of protein-encoding moiety of the DNA compound.

Proteins of particular interest which can be expressed by the current method include the following proteins: hemoglobin, alpha-interferon, erythropoeitin, granulocyte-colony stimulating factor, interleukin-3, tissue plasminogen activator, beta-interferon, gamma-interferon, interleukin-1, epidermal growth factor, Factor XIII, met-phe-trypsinogen, procarboxypeptidase B, Lys$^{B28}$Pro$^{B29}$-proinsulin, met-arg-proinsulin, and echinocandin B deacylase.

The naturally-occurring phthalyl amidase gene of *Xanthobacter agilis*, which is SEQ ID NO:6, is available on an 3.2 kb SacI-BamHI restriction fragment of plasmid pZPA600, which can be isolated from *Streptomyces lividans* TK23/pZPA600 by techniques well known in the art. *Streptomyces lividans* TK23/pZPA600 designates Streptomyces lividans strain TK23 which has been transformed with vector pZPA600.

Plasmid pZPA600 was derived by ligating SEQ ID NO:6 into Streptomyces vector, pIJ702 (Hopwood, D. A., Bibb, M. J., Smith, C. P., Ward, J. M., Schremph, H., *Genetic Manipulations of Streptomyces: A Laboratory Manual*, The John Innes Foundation, Norwich, England, 1985). The pIJ702 vector contains a pIJ101 Streptomyces replicon and a thiostrepton resistance gene for selection. The ligated material was transformed into *Streptomyces lividans* TK23 by a standard protoplast fusion technique. After selection on thiostrepton (45 µg/ml), the plasmid designated pZPA600, was isolated and confirmed by restriction analysis. A restriction site and function map of plasmid pZPA600 is found in FIG. 1.

*Streptomyces lividans* TK23/pZPA600 is publicly available and on deposit at the National Center for Agricultural Utilization Research, 1815 North University Street, Peoria, Ill. 61604-39999, under accession number NRRL B21290 (date of deposit: Jun. 23, 1994). The *Streptomyces lividans* TK23 strain has been previously described in *Plasmid* 12:1936 (1984).

Plasmid pZPA600, when transformed into *Streptomyces lividans* TK23, allows high level expression of the pro-phthalyl amidase ORF and results in secretion of soluble phthalyl amidase. Modification of plasmid pZPA600 by replacing the phthalyl amidase ORF by an ORF of an alternate protein results in secretion of the protein in soluble form. Thus, a preferred embodiment of the invention comprises a process in which *Streptomyces lividans* TK23, transformed by such a modified plasmid pZPA600, is grown and then separated from its extra-cellular broth so that high concentrations of the substituted protein are obtained in that cell-free broth.

The DNA sequences of the current invention may also be created by synthetic methodology. Such methodology of synthetic gene construction is well known in the art. See Brown et al. (1979) *Methods in Enzymology*, Academic Press, New York, 68:109. The DNA sequences may be generated using a conventional DNA synthesizing apparatus, such as the Applied Biosystems Model 380A of 380B DNA synthesizers (commercially available from Applied Biosystems, Inc., 850 Lincoln Center Drive, Foster City, Calif. 94404.

A skilled artisan will recognize that the nucleotide sequences described in the present disclosure may be altered by methods known in the art to produce additional sequences that substantially correspond to the described sequences without changing their functional aspects. These altered sequences are considered to be included in the current invention.

In order that the invention described herein may be more fully understood, the following examples are set forth. It should be understood that the examples are for illustrative purposes only and are not to be construed as limiting the scope of the invention.

EXAMPLE 1

Expression of pro-phthalyl amidase open reading frame in *Streptomyces lividans*

A 5 ml inoculum of *Streptomyces lividans* TK23/pZPA600 (grown for 48 hours at 30° C., 280 rpm) was added to each of two 2 L shake flasks containing 500 ml Trypticase Soy Broth medium and cultured at 30° C., 280 rpm for 24 hours. Incubations beyond 24 hours were deleterious to production of phthalyl amidase. Cells were removed by centrifugation (4° C., 15 min, 12,000× g). The cell-free broth (800 ml, 0.10 mg/ml) was passed at 1 ml/min through a Mono Q column (10×10 mm (8 ml); Pharmacia). A linear gradient of 0 to 1.5M KCl in buffer A was passed over the column and 2 ml fractions were collected. Most of the phthalyl amidase activity eluted in fractions 19 and 20 (about 0.75M KCl).

A 1 ml aliquot of fraction 19 was concentrated 10-fold via ultrafiltration and analyzed by SDS-PAGE. A major protein band was observed at about 50,000 daltons, which corresponded to the molecular weight observed by electrospray mass spectrometry for purified mature phthalyl amidase obtained from Xanthobacter agilis. It also corresponded closely to the theoretical molecular weight predicted for a protein encoded by SEQ ID NO:1.

Culturing Streptomyces lividans/pZPA600 under conditions promoting gene expression resulted in expression of 76,378 units of phthalyl amidase activity per liter of culture medium having a specific activity of 748.8 nmol/min/mg.

Phthalyl amidase activity was determined using phthalamido carbacephem (III) as substrate.

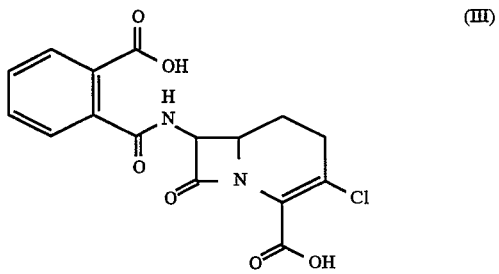

The enzymatic reaction was initiated by the addition of phthalyl amidase and stopped by the addition of 1 ml methanol. Specific activity of the enzyme was determined by monitoring the hydrolysis of III into the corresponding beta-lactam nucleus and phthalic acid by HPLC

EXAMPLE 2

Construction of a Phthalyl Amidase Signal Plasmid pZSIGPA

Creation of a plasmid (pZSIGPA) (FIG. 2) containing the phthalyl amidase promoter and signal sequence is as follows. Plasmid pZPA600 (NRRL B21290, date of deposit: Jun. 28, 1994) is digested with SacI and MluI to release a 1.08 kb fragment, which is subsequently excised from an agarose gel and eluted by the GeneClean method (Bio 101). The SacI-MluI fragment contains an internal XhoI site within the coding sequence for the phthalyl amidase signal peptide (see Example 6). The purified fragment is ligated into a prepared vector pUCBM20 (digested with SacI and MluI) and transformed into competant E. coli DH5α (BRL) using the supplied protocol. Ampicillin resistant clones are isolated and a clone containing pZSIGPA is confirmed by restriction analysis. All recombinant techniques in this and following examples employ standard protocols described in Sambrook, J., Fritsch, E. F., and Maniatis, T., (1989) *Molecular Cloning: A Laboratory Manual.* Cold Spring Harbor Laboratory Press, Cold Spring Harbor, N.Y.

EXAMPLE 3

Construction of XhoI-NdeI Linker

A DNA linker fragment, which encodes the carboxy-terminal portion of the Xanthobacter agilis phthalyl amidase signal peptide and which allows placement of any ORF having an NdeI overhang at the ATG start codon immediately downstream from the signal peptide cleavage sequence ALA-PHE-ALA is constructed according to the following procedure.

An 81 base pair oligonucleotide (SEQ. ID. NO: 13) is prepared and annealed with a 79 base pair DNA oligonucleotide (SEQ. ID. NO:14). Both oligonucleotides are synthesized on an ABI 380B DNA synthesizer and are purified with an Oligonucleotide Purification Cartridge®, (Applied Biosystems Inc., Foster City, Calif.).

The two oligonucleotides are mixed, heated to 80° C., and allowed to slowly cool to room temperature. In this manner the two oligonucleotides are annealed to form the desired double stranded linker having a four base overhang that appears at the 5' end of SEQ ID NO:13 and a two base overhang that appears at the 5' end of SEQ ID NO:14. This configuration results in XhoI and NdeI overhangs at opposite ends of the linker.

EXAMPLE 4

Isolation of the serine hydroxymethyltransferase (SHMT) ORF on an NdeI-BamHI fragment is done as follows. A plasmid which has been created to contain the SHMT ORF on an NdeI-BamHI fragment is digested with Ndei and BamHI to release a 1.41 kb fragment containing the SHMT ORF. The fragment is isolated and purified as in example 2.

EXAMPLE 5

Isolation of the p-nitrobenzyl esterase (PNB) ORF on a NdeI-BamHI fragment is done as follows. Plasmid pNB106R (constructed as described in patent application U.S. Ser. No. 08/124674, filed 20 Dec. 1994, herein incorporated by reference) is partially digested with NdeI and the linear plasmid is purified as in example 2. The linear fragment is digested with BamHI to release a 1.78 kb NdeI-BamHI fragment and isolated as in example 2.

EXAMPLE 6

Construction of intermediate plasmid pZSIGSHMT

Plasmid pZSIGPA (FIG. 3) is digested with XhoI and BamHI to release a 3.09 kb vector fragment, which is purified as in example 2. The XhoI end of the vector fragment encodes the amino-terminal portion of the phthalyl amidase signal peptide. The vector fragment is ligated to the XhoI-NdeI linker from example 3 and the NdeI-BamHI SHMT ORF fragment from example 4. The resulting plasmid mixture is transformed into E. coli DH5α (BRL) using the supplied protocol. Ampicillin resistant clones containing pZSIGSHMT are isolated and the correct plasmid is confirmed by restriction analysis.

EXAMPLE 7

Construction of plasmid pZSIGPNB

Plasmid pZSIGPA is digested with XhoI and BamHI to release a 3.09 kb vector fragment and the fragment is purified as in Example 2. The vector fragment is ligated to the XhoI-NdeI linker from Example 3 and the NdeI-BamHI PNB ORF fragment from example 5. The resulting plasmid mixture is transformed into E. coli DH5α (BRL) using the supplied protocol. Ampicillin resistant clones containing pZSIGPNB are isolated and the correct plasmid is confirmed by restriction analysis.

EXAMPLE 8

Construction of Expression Plasmid pSLSHMT and Transformation into *Streptomyces lividans*

Plasmid pZSIGSHMT is digested with SacI and BamHI to release a 1.83 kb fragment containing the phthalyl amidase promoter, signal sequence, and SHMT ORF. The fragment is purified as in example 2. This fragment is ligated to prepared vector pIJ702 (Hopwood, D. A., et. al., (1985) Genetic Manipulations of Streptomyces: *A Laboratory Manual*, The John Innes Foundation, Norwich, England.), digested with SacI and BglII and transformed into *Streptomyces lividans* TK23 using the protoplast fusion technique (Thompson, C. J., et al., (1982) Cloning of Antibiotic Resistance and Nutritional Genes in Streptomyces, J. Bacteriol. 151:668–77). Transformants are selected on thiostrepton (45 µg/ml). Plasmid DNA is isolated from a representative thiostrepton-resistant transformant and is analyzed by restriction enzyme analysis to verify that it is pSLSHMT.

EXAMPLE 9

Construction of Expression Plasmid pSLPNB and Transformation into *Streptomyces lividans*

Plasmid pZSIGPNB is digested with SacI and BamHI to release a 2.20 kb fragment containing the phthalyl amidase promoter, signal sequence, and PNB ORF. The fragment is purified as in example 2. This fragment is ligated to prepared vector pIJ702 (digested with SacI and BglII) and transformed into *Streptomyces lividans* TK23 using the protoplast fusion technique as done in Example 8. Transformants are selected on thiostrepton (45 µg/ml). Plasmid DNA is isolated from a representative thiostrepton-resistant transformant and is analyzed by restriction enzyme analysis to verify that it is pSLPNB.

EXAMPLE 10

Each pSP source plasmid listed in Table 1, Column 2 contains an ORF which is used in this invention to construct a corresponding pSL plasmid vector (Table 1, Column 4). Each source plasmid contains the ORF on an NdeI-BamHI fragment wherein the NdeI site comprises the ATG start codon of the ORF encoding a protein of interest (Table 1, Column 5) and the BamHI site is downstream of the ORF. A pSL plasmid vector is a vector that enables *Streptomyces lividans* to make and excrete the protein encoded by the source plasmid when the pSL vector is transformed into *Streptomyces lividans*. The pSL plasmid vectors are made via corresponding pZSIG intermediate plasmids (Table 1, Column 3). Each intermediate plasmid is constructed by digesting the corresponding source plasmid with NdeI and BamHI restriction enzymes and isolating the desired NdeI-BamHI fragment containing the ORF that encodes the protein of interest as in Example 2. The isolated fragment is used to replace the NdeI-BamHI fragment described for the construction of pZSIGSHMT in Example 6. In all other respects, construction of the intermediate plasmids is the same as pZSIGSHMT in Example 6.

Each pSL plasmid vector is constructed by digesting the corresponding intermediate plasmid with SacI and BamHI restriction enzymes. The SacI-BamHI fragment, which contains the ORF that encodes a fusion protein consisting of the *Xanthobacter agilis* phthalyl amidase signal peptide fused to the amino-terminus of the protein of interest, is isolated as in Example 2. The isolated fragment is used to replace the SacI-BamHI fragment described for the construction of pSLSHMT in Example 8. In all other respects, the construction of the pSL plasmid vectors is the same as the construction of pSLSHMT in Example 8.

TABLE 1

| Example | source plasmid | intermediate plasmid | plasmid vector | protein of interest |
|---|---|---|---|---|
| 10 | pSP603 | pZSIG603 | pSL603 | met-phe-trypsinogen |
| 11 | pSP213 | pZSIG213 | pSL213 | procarboxypeptidase B |
| 12 | pSP190 | pZSIG190 | pSL190 | $Lys^{B28}Pro^{B29}$-proinsulin |
| 13 | pSP182 | PZSIG182 | pSL182 | met-arg-proinsulin |

EXAMPLE 14

Expression of secreted SHMT by *Streptomyces lividans*/pSLSHMT, expression of secreted PNB esterase by *Streptomyces lividans*/pSLPNB, expression of secreted met-phe-trysinogen by *Streptomyces lividans*/pSL603, expression of secreted procarboxypeptidase B by *Streptomyces lividans*/pSL213, expression of secreted $Lys^{B28}Pro^{B29}$-proinsulin by *Streptomyces lividans*/pSL190, expression of secreted met-arg-proinsulin by *Streptomyces lividans*/pSL182, is carried out by fermentation as in Example 1. Assays specific for the protein of interest are used to determine the kinetics and extent of expression.

We claim:

1. A method for expressing protein, said method comprising:
   a) positioning a nucleotide sequence encoding said protein in a DNA vector adjacent to and downstream from a nucleotide sequence encoding a signal peptide SEQ ID NO:9 functional in *Streptomyces lividans;*
   b) transforming a host cell with said vector; and
   c) culturing said host cell under conditions suitable for gene expression, whereby said protein is secreted in soluble form.

2. The method of claim 1 wherein said nucleotide sequence encoding said signal peptide is SEQ ID NO:8.

3. The method of claim 1 wherein a promoter is positioned adjacent to and upstream from said nucleotide sequence encoding said signal peptide.

4. The method of claim 3 wherein said promoter is derived from a cell selected from the group consisting of *Xanthobacter agilis* and *Streptomyces lividans*.

5. The method of claim 4 wherein said promoter is SEQ ID NO:7.

6. The method of claim 5 wherein said nucleotide sequence encoding said protein encodes SEQ ID NO:2.

7. The method of claim 6 wherein said nucleotide sequence encoding said protein is SEQ ID NO:1.

8. The method of claim 1 wherein said host cell is *Streptomyces lividans*.

9. The method of claim 1 wherein said protein is known to be secreted in its natural host or in another surrogate host.

10. The method of claim 1 wherein said protein is known to exist as a part of a pro-protein consisting of a signal peptide amino acid sequence joined to the amino-terminus of the protein.

11. The method of claim 1 wherein said protein is encoded by a DNA compound comprising a nucleotide sequence encoding said signal peptide wherein said nucleotide sequence encoding said signal peptide is immediately adjacent to the carboxy-terminal end of a nucleotide sequence encoding said protein.

12. The method of claim 1 wherein said protein is selected from the group consisting of hemoglobin, alpha-interferon, erythropoeitin, granulocyte-colony stimulating factor, interleukin-3, tissue plasminogen activator, beta-interferon, gamma-interferon, interleukin-1, epidermal growth factor, Factor XIII, met-phe-trypsinogen, procarboxypeptidase B, $Lys^{B28}Pro^{B29}$-proinsulin, met-arg-proinsulin, and echinocandin B deacylase.

* * * * *

UNITED STATES PATENT AND TRADEMARK OFFICE
CERTIFICATE OF CORRECTION

PATENT NO. : 5,658,755

DATED : August 19, 1997

INVENTOR(S) : Queener and Zock

It is certified that error appears in the above-indentified patent and that said Letters Patent is hereby corrected as shown below:

Column 2, line 1, reads "...a clearable amino acid..."; should read "...a cleavable amino acid...".

Signed and Sealed this

Twenty-ninth Day of September, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 1359 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1356

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| CAG | GCG | CCG | TCT | GTG | CAC | CAA | CAC | GTC | GCC | TTC | ACT | GAG | GAA | ATT | GGA | 48 |
| Gln | Ala | Pro | Ser | Val | His | Gln | His | Val | Ala | Phe | Thr | Glu | Glu | Ile | Gly | |
| 1 | | | | 5 | | | | | 10 | | | | | 15 | | |
| GAC | CTT | CCC | GAC | GGC | TCA | AGT | TAC | ATG | ATC | CGT | GTG | CCG | GAG | AAC | TGG | 96 |
| Asp | Leu | Pro | Asp | Gly | Ser | Ser | Tyr | Met | Ile | Arg | Val | Pro | Glu | Asn | Trp | |
| | | | 20 | | | | | 25 | | | | | 30 | | | |
| AAC | GGC | GTG | TTA | ATT | CGC | GAC | CTA | GAC | CTT | GTC | AGC | GGC | ACC | AGC | AAT | 144 |
| Asn | Gly | Val | Leu | Ile | Arg | Asp | Leu | Asp | Leu | Val | Ser | Gly | Thr | Ser | Asn | |
| | | 35 | | | | | 40 | | | | | 45 | | | | |
| TCT | AAC | GCC | GCA | AGG | TAC | GAA | ACC | ATG | CTG | AAA | GAA | GGT | TTT | GCC | GTT | 192 |
| Ser | Asn | Ala | Ala | Arg | Tyr | Glu | Thr | Met | Leu | Lys | Glu | Gly | Phe | Ala | Val | |
| | 50 | | | | | 55 | | | | | 60 | | | | | |
| GCT | GGC | ACG | GCG | AGG | CAT | CCC | CTT | CGG | CAA | TGG | CAA | TAT | GAC | CCC | GCT | 240 |
| Ala | Gly | Thr | Ala | Arg | His | Pro | Leu | Arg | Gln | Trp | Gln | Tyr | Asp | Pro | Ala | |
| 65 | | | | | 70 | | | | | 75 | | | | | 80 | |
| CAC | GAG | ATT | GAA | AAC | CTC | AAT | CAC | GTG | CTG | GAC | ACA | TTC | GAG | GAA | AAT | 288 |
| His | Glu | Ile | Glu | Asn | Leu | Asn | His | Val | Leu | Asp | Thr | Phe | Glu | Glu | Asn | |
| | | | | 85 | | | | | 90 | | | | | 95 | | |
| TAC | GGT | TCA | CCT | GAA | AGA | GTT | ATC | CAG | TAC | GGT | TGC | TCG | GGT | GGG | GCA | 336 |
| Tyr | Gly | Ser | Pro | Glu | Arg | Val | Ile | Gln | Tyr | Gly | Cys | Ser | Gly | Gly | Ala | |
| | | | 100 | | | | | 105 | | | | | 110 | | | |
| CAC | GTG | TCA | CTA | GCC | GTG | GCA | GAG | GAC | TTC | TCG | GAC | CGC | GTA | GAT | GGC | 384 |
| His | Val | Ser | Leu | Ala | Val | Ala | Glu | Asp | Phe | Ser | Asp | Arg | Val | Asp | Gly | |
| | | 115 | | | | | 120 | | | | | 125 | | | | |
| TCA | GTT | GCT | CTA | GCT | GCT | CAT | ACT | CCT | GTC | TGG | ATA | ATG | AAT | TCT | TTC | 432 |
| Ser | Val | Ala | Leu | Ala | Ala | His | Thr | Pro | Val | Trp | Ile | Met | Asn | Ser | Phe | |
| | 130 | | | | | 135 | | | | | 140 | | | | | |
| TTG | GAC | GGA | TGG | TTT | TCG | CTG | CAG | TCT | CTG | ATC | GGC | GAG | TAC | TAT | GTA | 480 |
| Leu | Asp | Gly | Trp | Phe | Ser | Leu | Gln | Ser | Leu | Ile | Gly | Glu | Tyr | Tyr | Val | |
| 145 | | | | | 150 | | | | | 155 | | | | | 160 | |
| GAA | GCT | GGT | CAC | GGC | CCA | CTT | TCG | GAT | CTC | GCT | ATT | ACG | AAA | CTG | CCC | 528 |
| Glu | Ala | Gly | His | Gly | Pro | Leu | Ser | Asp | Leu | Ala | Ile | Thr | Lys | Leu | Pro | |
| | | | | 165 | | | | | 170 | | | | | 175 | | |
| AAT | GAT | GGT | AGC | TCT | AAT | TCG | AGC | GGT | CAT | GGA | ATG | GAA | GGA | GAT | CTT | 576 |
| Asn | Asp | Gly | Ser | Ser | Asn | Ser | Ser | Gly | His | Gly | Met | Glu | Gly | Asp | Leu | |
| | | | 180 | | | | | 185 | | | | | 190 | | | |
| CCT | GCC | GCG | TGG | CGC | AAC | GCG | TTC | ACC | GCT | GCT | AAC | GCC | ACA | CCT | GAG | 624 |
| Pro | Ala | Ala | Trp | Arg | Asn | Ala | Phe | Thr | Ala | Ala | Asn | Ala | Thr | Pro | Glu | |
| | | 195 | | | | | 200 | | | | | 205 | | | | |
| GGT | CGC | GCA | CGC | ATG | GCA | CTA | GCC | TTT | GCG | CTC | GGT | CAG | TGG | TCT | CCG | 672 |
| Gly | Arg | Ala | Arg | Met | Ala | Leu | Ala | Phe | Ala | Leu | Gly | Gln | Trp | Ser | Pro | |
| | 210 | | | | | 215 | | | | | 220 | | | | | |
| TGG | TTG | GCC | GAC | AAC | ACG | CCC | CAA | CCT | GAT | CTC | GAT | GAT | CCT | GAG | GCC | 720 |
| Trp | Leu | Ala | Asp | Asn | Thr | Pro | Gln | Pro | Asp | Leu | Asp | Asp | Pro | Glu | Ala | |
| 225 | | | | | 230 | | | | | 235 | | | | | 240 | |
| ATC | GCG | GAT | TCC | GTA | TAT | GAG | TCT | GCC | ATG | CGA | CTT | GCA | GGA | AGC | CCT | 768 |
| Ile | Ala | Asp | Ser | Val | Tyr | Glu | Ser | Ala | Met | Arg | Leu | Ala | Gly | Ser | Pro | |
| | | | | 245 | | | | | 250 | | | | | 255 | | |
| GGG | GGA | GAA | GCG | CGC | ATA | ATG | TTC | GAG | AAC | GCC | GCT | CGA | GGG | CAA | CAG | 816 |
| Gly | Gly | Glu | Ala | Arg | Ile | Met | Phe | Glu | Asn | Ala | Ala | Arg | Gly | Gln | Gln | |
| | | | 260 | | | | | 265 | | | | | 270 | | | |
| CTC | TCT | TGG | AAC | GAC | GAC | ATC | GAC | TAT | GCG | GAT | TTC | TGG | GAG | AAC | TCA | 864 |
| Leu | Ser | Trp | Asn | Asp | Asp | Ile | Asp | Tyr | Ala | Asp | Phe | Trp | Glu | Asn | Ser | |
| | | 275 | | | | | 280 | | | | | 285 | | | | |
| AAC | CCA | GCC | ATG | AAG | AGC | GCC | GTT | CAG | GAG | CTG | TAC | GAC | ACG | GCC | GGC | 912 |
| Asn | Pro | Ala | Met | Lys | Ser | Ala | Val | Gln | Glu | Leu | Tyr | Asp | Thr | Ala | Gly | |
| | 290 | | | | | 295 | | | | | 300 | | | | | |
| CTT | GAT | CTG | CAG | TCC | GAT | ATA | GAA | ACG | GTA | AAT | TCC | CAG | CCA | CGC | ATA | 960 |
| Leu | Asp | Leu | Gln | Ser | Asp | Ile | Glu | Thr | Val | Asn | Ser | Gln | Pro | Arg | Ile | |
| 305 | | | | | 310 | | | | | 315 | | | | | 320 | |

```
GAG GCA TCG CAG TAT GCG CTC GAC TAC TGG AAC ACG CCA GGT CGC AAT         1008
Glu Ala Ser Gln Tyr Ala Leu Asp Tyr Trp Asn Thr Pro Gly Arg Asn
            325                 330                 335

GTC ATT GGC GAC CCC GAA GTT CCT GTG CTG CGC CTG CAT ATG ATA GGC         1056
Val Ile Gly Asp Pro Glu Val Pro Val Leu Arg Leu His Met Ile Gly
            340                 345                 350

GAC TAC CAA ATT CCC TAT AGT CTT GTA CAG GGC TAC AGC GAT CTT ATC         1104
Asp Tyr Gln Ile Pro Tyr Ser Leu Val Gln Gly Tyr Ser Asp Leu Ile
            355                 360                 365

TCA GAG AAC AAC AAT GAT GAC TTG TAC AGA ACT GCT TTT GTG CAA TCC         1152
Ser Glu Asn Asn Asn Asp Asp Leu Tyr Arg Thr Ala Phe Val Gln Ser
            370                 375                 380

ACT GGA CAC TGC AAT TTC ACA GCT GCA GAA AGT TCC GCT GCG ATT GAG         1200
Thr Gly His Cys Asn Phe Thr Ala Ala Glu Ser Ser Ala Ala Ile Glu
385                 390                 395                 400

GTC ATG ATG CAA CGG CTT GAC ACG GGT GAG TGG CCG AGC ACC GAG CCG         1248
Val Met Met Gln Arg Leu Asp Thr Gly Glu Trp Pro Ser Thr Glu Pro
            405                 410                 415

GAT GAT CTG AAT GCA ATT GCC GAA GCC TCA AAC ACC GGA ACT GAA GCA         1296
Asp Asp Leu Asn Ala Ile Ala Glu Ala Ser Asn Thr Gly Thr Glu Ala
            420                 425                 430

CGT TTC ATG GCC CTA GAT GGC TGG GAA ATA CCC GAG TAC AAT CGT ACT         1344
Arg Phe Met Ala Leu Asp Gly Trp Glu Ile Pro Glu Tyr Asn Arg Thr
            435                 440                 445

TGG AAG CCT GAA TAA                                                     1359
Trp Lys Pro Glu
    450
```

( 2 ) INFORMATION FOR SEQ ID NO:2:

( i ) SEQUENCE CHARACTERISTICS:
        ( A ) LENGTH: 452 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Gln Ala Pro Ser Val His Gln His Val Ala Phe Thr Glu Glu Ile Gly
 1               5                   10                  15

Asp Leu Pro Asp Gly Ser Ser Tyr Met Ile Arg Val Pro Glu Asn Trp
            20                  25                  30

Asn Gly Val Leu Ile Arg Asp Leu Asp Leu Val Ser Gly Thr Ser Asn
            35                  40                  45

Ser Asn Ala Ala Arg Tyr Glu Thr Met Leu Lys Glu Gly Phe Ala Val
        50                  55                  60

Ala Gly Thr Ala Arg His Pro Leu Arg Gln Trp Gln Tyr Asp Pro Ala
65                  70                  75                  80

His Glu Ile Glu Asn Leu Asn His Val Leu Asp Thr Phe Glu Glu Asn
                85                  90                  95

Tyr Gly Ser Pro Glu Arg Val Ile Gln Tyr Gly Cys Ser Gly Gly Ala
            100                 105                 110

His Val Ser Leu Ala Val Ala Glu Asp Phe Ser Asp Arg Val Asp Gly
            115                 120                 125

Ser Val Ala Leu Ala Ala His Thr Pro Val Trp Ile Met Asn Ser Phe
        130                 135                 140

Leu Asp Gly Trp Phe Ser Leu Gln Ser Leu Ile Gly Glu Tyr Tyr Val
145                 150                 155                 160

Glu Ala Gly His Gly Pro Leu Ser Asp Leu Ala Ile Thr Lys Leu Pro
```

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |
| Asn | Asp | Gly | Ser | Ser | Asn | Ser | Ser | Gly | His | Gly | Met | Glu | Gly | Asp | Leu |
|     |     |     | 180 |     |     |     |     | 185 |     |     |     |     | 190 |     |     |
| Pro | Ala | Ala | Trp | Arg | Asn | Ala | Phe | Thr | Ala | Ala | Asn | Ala | Thr | Pro | Glu |
|     |     | 195 |     |     |     | 200 |     |     |     |     | 205 |     |     |     |     |
| Gly | Arg | Ala | Arg | Met | Ala | Leu | Ala | Phe | Ala | Leu | Gly | Gln | Trp | Ser | Pro |
|     | 210 |     |     |     |     | 215 |     |     |     |     | 220 |     |     |     |     |
| Trp | Leu | Ala | Asp | Asn | Thr | Pro | Gln | Pro | Asp | Leu | Asp | Asp | Pro | Glu | Ala |
| 225 |     |     |     |     | 230 |     |     |     |     | 235 |     |     |     |     | 240 |
| Ile | Ala | Asp | Ser | Val | Tyr | Glu | Ser | Ala | Met | Arg | Leu | Ala | Gly | Ser | Pro |
|     |     |     |     | 245 |     |     |     |     | 250 |     |     |     |     | 255 |     |
| Gly | Gly | Glu | Ala | Arg | Ile | Met | Phe | Glu | Asn | Ala | Ala | Arg | Gly | Gln | Gln |
|     |     |     | 260 |     |     |     |     | 265 |     |     |     |     | 270 |     |     |
| Leu | Ser | Trp | Asn | Asp | Asp | Ile | Asp | Tyr | Ala | Asp | Phe | Trp | Glu | Asn | Ser |
|     |     | 275 |     |     |     | 280 |     |     |     |     | 285 |     |     |     |     |
| Asn | Pro | Ala | Met | Lys | Ser | Ala | Val | Gln | Glu | Leu | Tyr | Asp | Thr | Ala | Gly |
|     |     | 290 |     |     |     | 295 |     |     |     |     | 300 |     |     |     |     |
| Leu | Asp | Leu | Gln | Ser | Asp | Ile | Glu | Thr | Val | Asn | Ser | Gln | Pro | Arg | Ile |
| 305 |     |     |     |     | 310 |     |     |     |     | 315 |     |     |     |     | 320 |
| Glu | Ala | Ser | Gln | Tyr | Ala | Leu | Asp | Tyr | Trp | Asn | Thr | Pro | Gly | Arg | Asn |
|     |     |     |     | 325 |     |     |     |     | 330 |     |     |     |     | 335 |     |
| Val | Ile | Gly | Asp | Pro | Glu | Val | Pro | Val | Leu | Arg | Leu | His | Met | Ile | Gly |
|     |     |     | 340 |     |     |     |     | 345 |     |     |     |     | 350 |     |     |
| Asp | Tyr | Gln | Ile | Pro | Tyr | Ser | Leu | Val | Gln | Gly | Tyr | Ser | Asp | Leu | Ile |
|     |     | 355 |     |     |     |     | 360 |     |     |     |     | 365 |     |     |     |
| Ser | Glu | Asn | Asn | Asn | Asp | Asp | Leu | Tyr | Arg | Thr | Ala | Phe | Val | Gln | Ser |
|     | 370 |     |     |     |     | 375 |     |     |     |     | 380 |     |     |     |     |
| Thr | Gly | His | Cys | Asn | Phe | Thr | Ala | Ala | Glu | Ser | Ser | Ala | Ala | Ile | Glu |
| 385 |     |     |     |     | 390 |     |     |     |     | 395 |     |     |     |     | 400 |
| Val | Met | Met | Gln | Arg | Leu | Asp | Thr | Gly | Glu | Trp | Pro | Ser | Thr | Glu | Pro |
|     |     |     |     | 405 |     |     |     |     | 410 |     |     |     |     | 415 |     |
| Asp | Asp | Leu | Asn | Ala | Ile | Ala | Glu | Ala | Ser | Asn | Thr | Gly | Thr | Glu | Ala |
|     |     |     | 420 |     |     |     |     | 425 |     |     |     |     | 430 |     |     |
| Arg | Phe | Met | Ala | Leu | Asp | Gly | Trp | Glu | Ile | Pro | Glu | Tyr | Asn | Arg | Thr |
|     |     | 435 |     |     |     |     | 440 |     |     |     |     | 445 |     |     |     |
| Trp | Lys | Pro | Glu |
|     | 450 |     |     |

(2) INFORMATION FOR SEQ ID NO:3:

(i) SEQUENCE CHARACTERISTICS:
        (A) LENGTH: 1485 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1482

(xi) SEQUENCE DESCRIPTION: SEQ ID NO:3:

| ATG | ATA | ATC | AAG | GGT | AGT | GTA | CCG | GGT | AAA | GCC | GGA | GGA | AAA | CCT | CGA | 48 |
| --- | --- | --- | --- | --- | --- | --- | --- | --- | --- | --- | --- | --- | --- | --- | --- | --- |
| Met | Ile | Ile | Lys | Gly | Ser | Val | Pro | Gly | Lys | Ala | Gly | Gly | Lys | Pro | Arg |     |
| 1   |     |     |     | 5   |     |     |     |     | 10  |     |     |     |     | 15  |     |     |
| GCG | ACC | ATC | TTT | CAT | AGT | TCT | ATT | GCA | ACG | CTA | CTT | TTA | ACC | ACA | GTC | 96 |
| Ala | Thr | Ile | Phe | His | Ser | Ser | Ile | Ala | Thr | Leu | Leu | Leu | Thr | Thr | Val |     |
|     |     |     | 20  |     |     |     |     | 25  |     |     |     |     | 30  |     |     |     |

```
TCA CTG TCA GGA GTA GCG CCA GCA TTT GCA CAG GCG CCG TCT GTG CAC        144
Ser Leu Ser Gly Val Ala Pro Ala Phe Ala Gln Ala Pro Ser Val His
        35                  40                  45

CAA CAC GTC GCC TTC ACT GAG GAA ATT GGA GAC CTT CCC GAC GGC TCA        192
Gln His Val Ala Phe Thr Glu Glu Ile Gly Asp Leu Pro Asp Gly Ser
 50                      55                  60

AGT TAC ATG ATC CGT GTG CCG GAG AAC TGG AAC GGC GTG TTA ATT CGC        240
Ser Tyr Met Ile Arg Val Pro Glu Asn Trp Asn Gly Val Leu Ile Arg
 65                      70                  75                  80

GAC CTA GAC CTT GTC AGC GGC ACC AGC AAT TCT AAC GCC GCA AGG TAC        288
Asp Leu Asp Leu Val Ser Gly Thr Ser Asn Ser Asn Ala Ala Arg Tyr
                 85                  90                  95

GAA ACC ATG CTG AAA GAA GGT TTT GCC GTT GCT GGC ACG GCG AGG CAT        336
Glu Thr Met Leu Lys Glu Gly Phe Ala Val Ala Gly Thr Ala Arg His
                100                 105                 110

CCC CTT CGG CAA TGG CAA TAT GAC CCC GCT CAC GAG ATT GAA AAC CTC        384
Pro Leu Arg Gln Trp Gln Tyr Asp Pro Ala His Glu Ile Glu Asn Leu
        115                 120                 125

AAT CAC GTG CTG GAC ACA TTC GAG GAA AAT TAC GGT TCA CCT GAA AGA        432
Asn His Val Leu Asp Thr Phe Glu Glu Asn Tyr Gly Ser Pro Glu Arg
130                 135                 140

GTT ATC CAG TAC GGT TGC TCG GGT GGG GCA CAC GTG TCA CTA GCC GTG        480
Val Ile Gln Tyr Gly Cys Ser Gly Gly Ala His Val Ser Leu Ala Val
145                 150                 155                 160

GCA GAG GAC TTC TCG GAC CGC GTA GAT GGC TCA GTT GCT CTA GCT GCT        528
Ala Glu Asp Phe Ser Asp Arg Val Asp Gly Ser Val Ala Leu Ala Ala
                165                 170                 175

CAT ACT CCT GTC TGG ATA ATG AAT TCT TTC TTG GAC GGA TGG TTT TCG        576
His Thr Pro Val Trp Ile Met Asn Ser Phe Leu Asp Gly Trp Phe Ser
                180                 185                 190

CTG CAG TCT CTG ATC GGC GAG TAC TAT GTA GAA GCT GGT CAC GGC CCA        624
Leu Gln Ser Leu Ile Gly Glu Tyr Tyr Val Glu Ala Gly His Gly Pro
        195                 200                 205

CTT TCG GAT CTC GCT ATT ACG AAA CTG CCC AAT GAT GGT AGC TCT AAT        672
Leu Ser Asp Leu Ala Ile Thr Lys Leu Pro Asn Asp Gly Ser Ser Asn
        210                 215                 220

TCG AGC GGT CAT GGA ATG GAA GGA GAT CTT CCT GCC GCG TGG CGC AAC        720
Ser Ser Gly His Gly Met Glu Gly Asp Leu Pro Ala Ala Trp Arg Asn
225                 230                 235                 240

GCG TTC ACC GCT GCT AAC GCC ACA CCT GAG GGT CGC GCA CGC ATG GCA        768
Ala Phe Thr Ala Ala Asn Ala Thr Pro Glu Gly Arg Ala Arg Met Ala
                245                 250                 255

CTA GCC TTT GCG CTC GGT CAG TGG TCT CCG TGG TTG GCC GAC AAC ACG        816
Leu Ala Phe Ala Leu Gly Gln Trp Ser Pro Trp Leu Ala Asp Asn Thr
                260                 265                 270

CCC CAA CCT GAT CTC GAT GAT CCT GAG GCC ATC GCG GAT TCC GTA TAT        864
Pro Gln Pro Asp Leu Asp Asp Pro Glu Ala Ile Ala Asp Ser Val Tyr
        275                 280                 285

GAG TCT GCC ATG CGA CTT GCA GGA AGC CCT GGG GGA GAA GCG CGC ATA        912
Glu Ser Ala Met Arg Leu Ala Gly Ser Pro Gly Gly Glu Ala Arg Ile
        290                 295                 300

ATG TTC GAG AAC GCC GCT CGA GGG CAA CAG CTC TCT TGG AAC GAC GAC        960
Met Phe Glu Asn Ala Ala Arg Gly Gln Gln Leu Ser Trp Asn Asp Asp
305                 310                 315                 320

ATC GAC TAT GCG GAT TTC TGG GAG AAC TCA AAC CCA GCC ATG AAG AGC       1008
Ile Asp Tyr Ala Asp Phe Trp Glu Asn Ser Asn Pro Ala Met Lys Ser
                325                 330                 335

GCC GTT CAG GAG CTG TAC GAC ACG GCC GGC CTT GAT CTG CAG TCC GAT       1056
Ala Val Gln Glu Leu Tyr Asp Thr Ala Gly Leu Asp Leu Gln Ser Asp
                340                 345                 350
```

| ATA | GAA | ACG | GTA | AAT | TCC | CAG | CCA | CGC | ATA | GAG | GCA | TCG | CAG | TAT | GCG | 1104 |
| Ile | Glu | Thr | Val | Asn | Ser | Gln | Pro | Arg | Ile | Glu | Ala | Ser | Gln | Tyr | Ala | |
|     |     | 355 |     |     |     |     | 360 |     |     |     |     | 365 |     |     |     | |

| CTC | GAC | TAC | TGG | AAC | ACG | CCA | GGT | CGC | AAT | GTC | ATT | GGC | GAC | CCC | GAA | 1152 |
| Leu | Asp | Tyr | Trp | Asn | Thr | Pro | Gly | Arg | Asn | Val | Ile | Gly | Asp | Pro | Glu | |
|     | 370 |     |     |     |     | 375 |     |     |     |     | 380 |     |     |     |     | |

| GTT | CCT | GTG | CTG | CGC | CTG | CAT | ATG | ATA | GGC | GAC | TAC | CAA | ATT | CCC | TAT | 1200 |
| Val | Pro | Val | Leu | Arg | Leu | His | Met | Ile | Gly | Asp | Tyr | Gln | Ile | Pro | Tyr | |
| 385 |     |     |     | 390 |     |     |     |     | 395 |     |     |     |     |     | 400 | |

| AGT | CTT | GTA | CAG | GGC | TAC | AGC | GAT | CTT | ATC | TCA | GAG | AAC | AAC | AAT | GAT | 1248 |
| Ser | Leu | Val | Gln | Gly | Tyr | Ser | Asp | Leu | Ile | Ser | Glu | Asn | Asn | Asn | Asp | |
|     |     |     |     | 405 |     |     |     |     | 410 |     |     |     |     | 415 |     | |

| GAC | TTG | TAC | AGA | ACT | GCT | TTT | GTG | CAA | TCC | ACT | GGA | CAC | TGC | AAT | TTC | 1296 |
| Asp | Leu | Tyr | Arg | Thr | Ala | Phe | Val | Gln | Ser | Thr | Gly | His | Cys | Asn | Phe | |
|     |     |     | 420 |     |     |     |     | 425 |     |     |     |     | 430 |     |     | |

| ACA | GCT | GCA | GAA | AGT | TCC | GCT | GCG | ATT | GAG | GTC | ATG | ATG | CAA | CGG | CTT | 1344 |
| Thr | Ala | Ala | Glu | Ser | Ser | Ala | Ala | Ile | Glu | Val | Met | Met | Gln | Arg | Leu | |
|     |     | 435 |     |     |     |     | 440 |     |     |     |     | 445 |     |     |     | |

| GAC | ACG | GGT | GAG | TGG | CCG | AGC | ACC | GAG | CCG | GAT | GAT | CTG | AAT | GCA | ATT | 1392 |
| Asp | Thr | Gly | Glu | Trp | Pro | Ser | Thr | Glu | Pro | Asp | Asp | Leu | Asn | Ala | Ile | |
|     | 450 |     |     |     |     | 455 |     |     |     |     | 460 |     |     |     |     | |

| GCC | GAA | GCC | TCA | AAC | ACC | GGA | ACT | GAA | GCA | CGT | TTC | ATG | GCC | CTA | GAT | 1440 |
| Ala | Glu | Ala | Ser | Asn | Thr | Gly | Thr | Glu | Ala | Arg | Phe | Met | Ala | Leu | Asp | |
| 465 |     |     |     |     | 470 |     |     |     |     | 475 |     |     |     |     | 480 | |

| GGC | TGG | GAA | ATA | CCC | GAG | TAC | AAT | CGT | ACT | TGG | AAG | CCT | GAA | TAA |   | 1485 |
| Gly | Trp | Glu | Ile | Pro | Glu | Tyr | Asn | Arg | Thr | Trp | Lys | Pro | Glu |     |   | |
|     |     |     |     | 485 |     |     |     |     | 490 |     |     |     |     |     |   | |

( 2 ) INFORMATION FOR SEQ ID NO:4:

( i ) SEQUENCE CHARACTERISTICS:
        ( A ) LENGTH: 494 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Ile | Ile | Lys | Gly | Ser | Val | Pro | Gly | Lys | Ala | Gly | Gly | Lys | Pro | Arg |
| 1   |     |     |     | 5   |     |     |     |     | 10  |     |     |     |     | 15  |     |

| Ala | Thr | Ile | Phe | His | Ser | Ser | Ile | Ala | Thr | Leu | Leu | Leu | Thr | Thr | Val |
|     |     |     | 20  |     |     |     |     | 25  |     |     |     |     | 30  |     |     |

| Ser | Leu | Ser | Gly | Val | Ala | Pro | Ala | Phe | Ala | Gln | Ala | Pro | Ser | Val | His |
|     |     | 35  |     |     |     |     | 40  |     |     |     |     | 45  |     |     |     |

| Gln | His | Val | Ala | Phe | Thr | Glu | Glu | Ile | Gly | Asp | Leu | Pro | Asp | Gly | Ser |
|     | 50  |     |     |     |     | 55  |     |     |     |     | 60  |     |     |     |     |

| Ser | Tyr | Met | Ile | Arg | Val | Pro | Glu | Asn | Trp | Asn | Gly | Val | Leu | Ile | Arg |
| 65  |     |     |     |     | 70  |     |     |     |     | 75  |     |     |     |     | 80  |

| Asp | Leu | Asp | Leu | Val | Ser | Gly | Thr | Ser | Asn | Ser | Asn | Ala | Ala | Arg | Tyr |
|     |     |     |     | 85  |     |     |     |     | 90  |     |     |     |     | 95  |     |

| Glu | Thr | Met | Leu | Lys | Glu | Gly | Phe | Ala | Val | Ala | Gly | Thr | Ala | Arg | His |
|     |     |     | 100 |     |     |     |     | 105 |     |     |     |     | 110 |     |     |

| Pro | Leu | Arg | Gln | Trp | Gln | Tyr | Asp | Pro | Ala | His | Glu | Ile | Glu | Asn | Leu |
|     |     | 115 |     |     |     |     | 120 |     |     |     |     | 125 |     |     |     |

| Asn | His | Val | Leu | Asp | Thr | Phe | Glu | Glu | Asn | Tyr | Gly | Ser | Pro | Glu | Arg |
|     | 130 |     |     |     |     | 135 |     |     |     |     | 140 |     |     |     |     |

| Val | Ile | Gln | Tyr | Gly | Cys | Ser | Gly | Gly | Ala | His | Val | Ser | Leu | Ala | Val |
| 145 |     |     |     |     | 150 |     |     |     |     | 155 |     |     |     |     | 160 |

| Ala | Glu | Asp | Phe | Ser | Asp | Arg | Val | Asp | Gly | Ser | Val | Ala | Leu | Ala | Ala |

|     |     |     |     |     | 165 |     |     |     | 170 |     |     |     |     | 175 |     |
| --- | --- | --- | --- | --- | --- | --- | --- | --- | --- | --- | --- | --- | --- | --- | --- |
| His | Thr | Pro | Val<br>180 | Trp | Ile | Met | Asn | Ser<br>185 | Phe | Leu | Asp | Gly | Trp<br>190 | Phe | Ser |
| Leu | Gln | Ser<br>195 | Leu | Ile | Gly | Glu | Tyr<br>200 | Tyr | Val | Glu | Ala | Gly<br>205 | His | Gly | Pro |
| Leu | Ser | Asp<br>210 | Leu | Ala | Ile | Thr<br>215 | Lys | Leu | Pro | Asn | Asp<br>220 | Gly | Ser | Ser | Asn |
| Ser<br>225 | Ser | Gly | His | Gly | Met<br>230 | Glu | Gly | Asp | Leu | Pro<br>235 | Ala | Ala | Trp | Arg | Asn<br>240 |
| Ala | Phe | Thr | Ala | Ala<br>245 | Asn | Ala | Thr | Pro | Glu<br>250 | Gly | Arg | Ala | Arg | Met<br>255 | Ala |
| Leu | Ala | Phe | Ala<br>260 | Leu | Gly | Gln | Trp | Ser<br>265 | Pro | Trp | Leu | Ala | Asp<br>270 | Asn | Thr |
| Pro | Gln | Pro<br>275 | Asp | Leu | Asp | Asp | Pro<br>280 | Glu | Ala | Ile | Ala | Asp<br>285 | Ser | Val | Tyr |
| Glu | Ser<br>290 | Ala | Met | Arg | Leu | Ala<br>295 | Gly | Ser | Pro | Gly | Gly<br>300 | Glu | Ala | Arg | Ile |
| Met<br>305 | Phe | Glu | Asn | Ala | Ala<br>310 | Arg | Gly | Gln | Gln | Leu<br>315 | Ser | Trp | Asn | Asp | Asp<br>320 |
| Ile | Asp | Tyr | Ala | Asp<br>325 | Phe | Trp | Glu | Asn | Ser<br>330 | Asn | Pro | Ala | Met | Lys<br>335 | Ser |
| Ala | Val | Gln | Glu<br>340 | Leu | Tyr | Asp | Thr | Ala<br>345 | Gly | Leu | Asp | Leu | Gln<br>350 | Ser | Asp |
| Ile | Glu | Thr<br>355 | Val | Asn | Ser | Gln | Pro<br>360 | Arg | Ile | Glu | Ala | Ser<br>365 | Gln | Tyr | Ala |
| Leu | Asp<br>370 | Tyr | Trp | Asn | Thr | Pro<br>375 | Gly | Arg | Asn | Val | Ile<br>380 | Gly | Asp | Pro | Glu |
| Val<br>385 | Pro | Val | Leu | Arg | Leu<br>390 | His | Met | Ile | Gly | Asp<br>395 | Tyr | Gln | Ile | Pro | Tyr<br>400 |
| Ser | Leu | Val | Gln | Gly<br>405 | Tyr | Ser | Asp | Leu | Ile<br>410 | Ser | Glu | Asn | Asn | Asn<br>415 | Asp |
| Asp | Leu | Tyr | Arg<br>420 | Thr | Ala | Phe | Val | Gln<br>425 | Ser | Thr | Gly | His | Cys<br>430 | Asn | Phe |
| Thr | Ala | Ala<br>435 | Glu | Ser | Ser | Ala | Ala<br>440 | Ile | Glu | Val | Met | Met<br>445 | Gln | Arg | Leu |
| Asp | Thr<br>450 | Gly | Glu | Trp | Pro | Ser<br>455 | Thr | Glu | Pro | Asp | Asp<br>460 | Leu | Asn | Ala | Ile |
| Ala<br>465 | Glu | Ala | Ser | Asn | Thr<br>470 | Gly | Thr | Glu | Ala | Arg<br>475 | Phe | Met | Ala | Leu | Asp<br>480 |
| Gly | Trp | Glu | Ile | Pro<br>485 | Glu | Tyr | Asn | Arg | Thr<br>490 | Trp | Lys | Pro | Glu |     |     |

( 2 ) INFORMATION FOR SEQ ID NO:5:

( i ) SEQUENCE CHARACTERISTICS:
        ( A ) LENGTH: 1620 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 136..1617

( x i ) SEQUENCE DESCRIPTION: SEQ ID NO:5:

GGATCCTTAG GAATCTAAAC ATTCTGGTTG ACACTCCACA TTTTGAATGT CAGCATTTCG     60

| | | | | | | | | | | |
|---|---|---|---|---|---|---|---|---|---|---|
| GCCATGGCTG | CTATGCAGCC | TGTTATTGCA | TTTGAAATGG | AATAGATCAG | CAAACTTATC | | | | | 120 |
| GGGAGGATGA | GTATT | ATG | ATA | ATC | AAG | GGT | AGT | GTA | CCG GGT AAA GCC GGA | 171 |
| | | Met | Ile | Ile | Lys | Gly | Ser | Val | Pro Gly Lys Ala Gly | |
| | | 1 | | | 5 | | | | 10 | |

| | | | | | | | | | | | | | | | |
|---|---|---|---|---|---|---|---|---|---|---|---|---|---|---|---|
| GGA | AAA | CCT | CGA | GCG | ACC | ATC | TTT | CAT | AGT | TCT | ATT | GCA | ACG | CTA CTT | 219 |
| Gly | Lys | Pro | Arg | Ala | Thr | Ile | Phe | His | Ser | Ser | Ile | Ala | Thr | Leu Leu | |
| | | 15 | | | | 20 | | | | 25 | | | | | |
| TTA | ACC | ACA | GTC | TCA | CTG | TCA | GGA | GTA | GCG | CCA | GCA | TTT | GCA | CAG GCG | 267 |
| Leu | Thr | Thr | Val | Ser | Leu | Ser | Gly | Val | Ala | Pro | Ala | Phe | Ala | Gln Ala | |
| | 30 | | | | 35 | | | | 40 | | | | | | |
| CCG | TCT | GTG | CAC | CAA | CAC | GTC | GCC | TTC | ACT | GAG | GAA | ATT | GGA | GAC CTT | 315 |
| Pro | Ser | Val | His | Gln | His | Val | Ala | Phe | Thr | Glu | Glu | Ile | Gly | Asp Leu | |
| 45 | | | | 50 | | | | 55 | | | | | | 60 | |
| CCC | GAC | GGC | TCA | AGT | TAC | ATG | ATC | CGT | GTG | CCG | GAG | AAC | TGG | AAC GGC | 363 |
| Pro | Asp | Gly | Ser | Ser | Tyr | Met | Ile | Arg | Val | Pro | Glu | Asn | Trp | Asn Gly | |
| | | | | 65 | | | | 70 | | | | | 75 | | |
| GTG | TTA | ATT | CGC | GAC | CTA | GAC | CTT | GTC | AGC | GGC | ACC | AGC | AAT | TCT AAC | 411 |
| Val | Leu | Ile | Arg | Asp | Leu | Asp | Leu | Val | Ser | Gly | Thr | Ser | Asn | Ser Asn | |
| | | | 80 | | | | 85 | | | | | 90 | | | |
| GCC | GCA | AGG | TAC | GAA | ACC | ATG | CTG | AAA | GAA | GGT | TTT | GCC | GTT | GCT GGC | 459 |
| Ala | Ala | Arg | Tyr | Glu | Thr | Met | Leu | Lys | Glu | Gly | Phe | Ala | Val | Ala Gly | |
| | | 95 | | | | 100 | | | | 105 | | | | | |
| ACG | GCG | AGG | CAT | CCC | CTT | CGG | CAA | TGG | CAA | TAT | GAC | CCC | GCT | CAC GAG | 507 |
| Thr | Ala | Arg | His | Pro | Leu | Arg | Gln | Trp | Gln | Tyr | Asp | Pro | Ala | His Glu | |
| | 110 | | | | 115 | | | | 120 | | | | | | |
| ATT | GAA | AAC | CTC | AAT | CAC | GTG | CTG | GAC | ACA | TTC | GAG | GAA | AAT | TAC GGT | 555 |
| Ile | Glu | Asn | Leu | Asn | His | Val | Leu | Asp | Thr | Phe | Glu | Glu | Asn | Tyr Gly | |
| 125 | | | | 130 | | | | 135 | | | | | | 140 | |
| TCA | CCT | GAA | AGA | GTT | ATC | CAG | TAC | GGT | TGC | TCG | GGT | GGG | GCA | CAC GTG | 603 |
| Ser | Pro | Glu | Arg | Val | Ile | Gln | Tyr | Gly | Cys | Ser | Gly | Gly | Ala | His Val | |
| | | | 145 | | | | 150 | | | | | 155 | | | |
| TCA | CTA | GCC | GTG | GCA | GAG | GAC | TTC | TCG | GAC | CGC | GTA | GAT | GGC | TCA GTT | 651 |
| Ser | Leu | Ala | Val | Ala | Glu | Asp | Phe | Ser | Asp | Arg | Val | Asp | Gly | Ser Val | |
| | | | 160 | | | | 165 | | | | | 170 | | | |
| GCT | CTA | GCT | GCT | CAT | ACT | CCT | GTC | TGG | ATA | ATG | AAT | TCT | TTC | TTG GAC | 699 |
| Ala | Leu | Ala | Ala | His | Thr | Pro | Val | Trp | Ile | Met | Asn | Ser | Phe | Leu Asp | |
| | | 175 | | | | 180 | | | | 185 | | | | | |
| GGA | TGG | TTT | TCG | CTG | CAG | TCT | CTG | ATC | GGC | GAG | TAC | TAT | GTA | GAA GCT | 747 |
| Gly | Trp | Phe | Ser | Leu | Gln | Ser | Leu | Ile | Gly | Glu | Tyr | Tyr | Val | Glu Ala | |
| | 190 | | | | 195 | | | | 200 | | | | | | |
| GGT | CAC | GGC | CCA | CTT | TCG | GAT | CTC | GCT | ATT | ACG | AAA | CTG | CCC | AAT GAT | 795 |
| Gly | His | Gly | Pro | Leu | Ser | Asp | Leu | Ala | Ile | Thr | Lys | Leu | Pro | Asn Asp | |
| 205 | | | | 210 | | | | 215 | | | | | | 220 | |
| GGT | AGC | TCT | AAT | TCG | AGC | GGT | CAT | GGA | ATG | GAA | GGA | GAT | CTT | CCT GCC | 843 |
| Gly | Ser | Ser | Asn | Ser | Ser | Gly | His | Gly | Met | Glu | Gly | Asp | Leu | Pro Ala | |
| | | | | 225 | | | | 230 | | | | | 235 | | |
| GCG | TGG | CGC | AAC | GCG | TTC | ACC | GCT | GCT | AAC | GCC | ACA | CCT | GAG | GGT CGC | 891 |
| Ala | Trp | Arg | Asn | Ala | Phe | Thr | Ala | Ala | Asn | Ala | Thr | Pro | Glu | Gly Arg | |
| | | | 240 | | | | 245 | | | | | 250 | | | |
| GCA | CGC | ATG | GCA | CTA | GCC | TTT | GCG | CTC | GGT | CAG | TGG | TCT | CCG | TGG TTG | 939 |
| Ala | Arg | Met | Ala | Leu | Ala | Phe | Ala | Leu | Gly | Gln | Trp | Ser | Pro | Trp Leu | |
| | | 255 | | | | 260 | | | | 265 | | | | | |
| GCC | GAC | AAC | ACG | CCC | CAA | CCT | GAT | CTC | GAT | GAT | CCT | GAG | GCC | ATC GCG | 987 |
| Ala | Asp | Asn | Thr | Pro | Gln | Pro | Asp | Leu | Asp | Asp | Pro | Glu | Ala | Ile Ala | |
| | 270 | | | | 275 | | | | 280 | | | | | | |
| GAT | TCC | GTA | TAT | GAG | TCT | GCC | ATG | CGA | CTT | GCA | GGA | AGC | CCT | GGG GGA | 1035 |
| Asp | Ser | Val | Tyr | Glu | Ser | Ala | Met | Arg | Leu | Ala | Gly | Ser | Pro | Gly Gly | |
| 285 | | | | 290 | | | | 295 | | | | | | 300 | |

| | | | | | | | | | | | | | | | | |
|---|---|---|---|---|---|---|---|---|---|---|---|---|---|---|---|---|
| GAA | GCG | CGC | ATA | ATG | TTC | GAG | AAC | GCC | GCT | CGA | GGG | CAA | CAG | CTC | TCT | 1083 |
| Glu | Ala | Arg | Ile | Met | Phe | Glu | Asn | Ala | Ala | Arg | Gly | Gln | Gln | Leu | Ser | |
| | | | | 305 | | | | | 310 | | | | | 315 | | |
| TGG | AAC | GAC | GAC | ATC | GAC | TAT | GCG | GAT | TTC | TGG | GAG | AAC | TCA | AAC | CCA | 1131 |
| Trp | Asn | Asp | Asp | Ile | Asp | Tyr | Ala | Asp | Phe | Trp | Glu | Asn | Ser | Asn | Pro | |
| | | | 320 | | | | | 325 | | | | | 330 | | | |
| GCC | ATG | AAG | AGC | GCC | GTT | CAG | GAG | CTG | TAC | GAC | ACG | GCC | GGC | CTT | GAT | 1179 |
| Ala | Met | Lys | Ser | Ala | Val | Gln | Glu | Leu | Tyr | Asp | Thr | Ala | Gly | Leu | Asp | |
| | | 335 | | | | | 340 | | | | | 345 | | | | |
| CTG | CAG | TCC | GAT | ATA | GAA | ACG | GTA | AAT | TCC | CAG | CCA | CGC | ATA | GAG | GCA | 1227 |
| Leu | Gln | Ser | Asp | Ile | Glu | Thr | Val | Asn | Ser | Gln | Pro | Arg | Ile | Glu | Ala | |
| | 350 | | | | | 355 | | | | | 360 | | | | | |
| TCG | CAG | TAT | GCG | CTC | GAC | TAC | TGG | AAC | ACG | CCA | GGT | CGC | AAT | GTC | ATT | 1275 |
| Ser | Gln | Tyr | Ala | Leu | Asp | Tyr | Trp | Asn | Thr | Pro | Gly | Arg | Asn | Val | Ile | |
| 365 | | | | | 370 | | | | | 375 | | | | | 380 | |
| GGC | GAC | CCC | GAA | GTT | CCT | GTG | CTG | CGC | CTG | CAT | ATG | ATA | GGC | GAC | TAC | 1323 |
| Gly | Asp | Pro | Glu | Val | Pro | Val | Leu | Arg | Leu | His | Met | Ile | Gly | Asp | Tyr | |
| | | | | 385 | | | | | 390 | | | | | 395 | | |
| CAA | ATT | CCC | TAT | AGT | CTT | GTA | CAG | GGC | TAC | AGC | GAT | CTT | ATC | TCA | GAG | 1371 |
| Gln | Ile | Pro | Tyr | Ser | Leu | Val | Gln | Gly | Tyr | Ser | Asp | Leu | Ile | Ser | Glu | |
| | | | 400 | | | | | 405 | | | | | 410 | | | |
| AAC | AAC | AAT | GAT | GAC | TTG | TAC | AGA | ACT | GCT | TTT | GTG | CAA | TCC | ACT | GGA | 1419 |
| Asn | Asn | Asn | Asp | Asp | Leu | Tyr | Arg | Thr | Ala | Phe | Val | Gln | Ser | Thr | Gly | |
| | | 415 | | | | | 420 | | | | | 425 | | | | |
| CAC | TGC | AAT | TTC | ACA | GCT | GCA | GAA | AGT | TCC | GCT | GCG | ATT | GAG | GTC | ATG | 1467 |
| His | Cys | Asn | Phe | Thr | Ala | Ala | Glu | Ser | Ser | Ala | Ala | Ile | Glu | Val | Met | |
| | 430 | | | | | 435 | | | | | 440 | | | | | |
| ATG | CAA | CGG | CTT | GAC | ACG | GGT | GAG | TGG | CCG | AGC | ACC | GAG | CCG | GAT | GAT | 1515 |
| Met | Gln | Arg | Leu | Asp | Thr | Gly | Glu | Trp | Pro | Ser | Thr | Glu | Pro | Asp | Asp | |
| 445 | | | | | 450 | | | | | 455 | | | | | 460 | |
| CTG | AAT | GCA | ATT | GCC | GAA | GCC | TCA | AAC | ACC | GGA | ACT | GAA | GCA | CGT | TTC | 1563 |
| Leu | Asn | Ala | Ile | Ala | Glu | Ala | Ser | Asn | Thr | Gly | Thr | Glu | Ala | Arg | Phe | |
| | | | | 465 | | | | | 470 | | | | | 475 | | |
| ATG | GCC | CTA | GAT | GGC | TGG | GAA | ATA | CCC | GAG | TAC | AAT | CGT | ACT | TGG | AAG | 1611 |
| Met | Ala | Leu | Asp | Gly | Trp | Glu | Ile | Pro | Glu | Tyr | Asn | Arg | Thr | Trp | Lys | |
| | | | 480 | | | | | 485 | | | | | 490 | | | |
| CCT | GAA | TAA | | | | | | | | | | | | | | 1620 |
| Pro | Glu | | | | | | | | | | | | | | | |

( 2 ) INFORMATION FOR SEQ ID NO:6:

( i ) SEQUENCE CHARACTERISTICS:
        ( A ) LENGTH: 3029 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 136..1617

( x i ) SEQUENCE DESCRIPTION: SEQ ID NO:6:

| | | | | | | |
|---|---|---|---|---|---|---|
| GGATCCTTAG | GAATCTAAAC | ATTCTGGTTG | ACACTCCACA | TTTTGAATGT | CAGCATTTCG | 60 |
| GCCATGGCTG | CTATGCAGCC | TGTTATTGCA | TTTGAAATGG | AATAGATCAG | CAAACTTATC | 120 |
| GGGAGGATGA | GTATT ATG | ATA ATC | AAG GGT | AGT GTA | CCG GGT AAA GCC GGA | 171 |

| | | | | | | | | | | | | | | | | |
|---|---|---|---|---|---|---|---|---|---|---|---|---|---|---|---|---|
| | | | | Met | Ile | Ile | Lys | Gly | Ser | Val | Pro | Gly | Lys | Ala | Gly | |
| | | | | 1 | | | | 5 | | | | | 10 | | | |
| GGA | AAA | CCT | CGA | GCG | ACC | ATC | TTT | CAT | AGT | TCT | ATT | GCA | ACG | CTA | CTT | 219 |
| Gly | Lys | Pro | Arg | Ala | Thr | Ile | Phe | His | Ser | Ser | Ile | Ala | Thr | Leu | Leu | |
| | 15 | | | | | 20 | | | | | 25 | | | | | |

-continued

| | | | | | | | | | | | | | | | | |
|---|---|---|---|---|---|---|---|---|---|---|---|---|---|---|---|---|
| TTA | ACC | ACA | GTC | TCA | CTG | TCA | GGA | GTA | GCG | CCA | GCA | TTT | GCA | CAG | GCG | 267 |
| Leu | Thr | Thr | Val | Ser | Leu | Ser | Gly | Val | Ala | Pro | Ala | Phe | Ala | Gln | Ala | |
| | 30 | | | | 35 | | | | | 40 | | | | | | |
| CCG | TCT | GTG | CAC | CAA | CAC | GTC | GCC | TTC | ACT | GAG | GAA | ATT | GGA | GAC | CTT | 315 |
| Pro | Ser | Val | His | Gln | His | Val | Ala | Phe | Thr | Glu | Glu | Ile | Gly | Asp | Leu | |
| 45 | | | | 50 | | | | | 55 | | | | | | 60 | |
| CCC | GAC | GGC | TCA | AGT | TAC | ATG | ATC | CGT | GTG | CCG | GAG | AAC | TGG | AAC | GGC | 363 |
| Pro | Asp | Gly | Ser | Ser | Tyr | Met | Ile | Arg | Val | Pro | Glu | Asn | Trp | Asn | Gly | |
| | | | | 65 | | | | | 70 | | | | | 75 | | |
| GTG | TTA | ATT | CGC | GAC | CTA | GAC | CTT | GTC | AGC | GGC | ACC | AGC | AAT | TCT | AAC | 411 |
| Val | Leu | Ile | Arg | Asp | Leu | Asp | Leu | Val | Ser | Gly | Thr | Ser | Asn | Ser | Asn | |
| | | | 80 | | | | | 85 | | | | | 90 | | | |
| GCC | GCA | AGG | TAC | GAA | ACC | ATG | CTG | AAA | GAA | GGT | TTT | GCC | GTT | GCT | GGC | 459 |
| Ala | Ala | Arg | Tyr | Glu | Thr | Met | Leu | Lys | Glu | Gly | Phe | Ala | Val | Ala | Gly | |
| | | 95 | | | | | 100 | | | | | 105 | | | | |
| ACG | GCG | AGG | CAT | CCC | CTT | CGG | CAA | TGG | CAA | TAT | GAC | CCC | GCT | CAC | GAG | 507 |
| Thr | Ala | Arg | His | Pro | Leu | Arg | Gln | Trp | Gln | Tyr | Asp | Pro | Ala | His | Glu | |
| | 110 | | | | | 115 | | | | | 120 | | | | | |
| ATT | GAA | AAC | CTC | AAT | CAC | GTG | CTG | GAC | ACA | TTC | GAG | GAA | AAT | TAC | GGT | 555 |
| Ile | Glu | Asn | Leu | Asn | His | Val | Leu | Asp | Thr | Phe | Glu | Glu | Asn | Tyr | Gly | |
| 125 | | | | | 130 | | | | | 135 | | | | | 140 | |
| TCA | CCT | GAA | AGA | GTT | ATC | CAG | TAC | GGT | TGC | TCG | GGT | GGG | GCA | CAC | GTG | 603 |
| Ser | Pro | Glu | Arg | Val | Ile | Gln | Tyr | Gly | Cys | Ser | Gly | Gly | Ala | His | Val | |
| | | | | 145 | | | | | 150 | | | | | 155 | | |
| TCA | CTA | GCC | GTG | GCA | GAG | GAC | TTC | TCG | GAC | CGC | GTA | GAT | GGC | TCA | GTT | 651 |
| Ser | Leu | Ala | Val | Ala | Glu | Asp | Phe | Ser | Asp | Arg | Val | Asp | Gly | Ser | Val | |
| | | | 160 | | | | | 165 | | | | | 170 | | | |
| GCT | CTA | GCT | GCT | CAT | ACT | CCT | GTC | TGG | ATA | ATG | AAT | TCT | TTC | TTG | GAC | 699 |
| Ala | Leu | Ala | Ala | His | Thr | Pro | Val | Trp | Ile | Met | Asn | Ser | Phe | Leu | Asp | |
| | | 175 | | | | | 180 | | | | | 185 | | | | |
| GGA | TGG | TTT | TCG | CTG | CAG | TCT | CTG | ATC | GGC | GAG | TAC | TAT | GTA | GAA | GCT | 747 |
| Gly | Trp | Phe | Ser | Leu | Gln | Ser | Leu | Ile | Gly | Glu | Tyr | Tyr | Val | Glu | Ala | |
| | 190 | | | | | 195 | | | | | 200 | | | | | |
| GGT | CAC | GGC | CCA | CTT | TCG | GAT | CTC | GCT | ATT | ACG | AAA | CTG | CCC | AAT | GAT | 795 |
| Gly | His | Gly | Pro | Leu | Ser | Asp | Leu | Ala | Ile | Thr | Lys | Leu | Pro | Asn | Asp | |
| 205 | | | | | 210 | | | | | 215 | | | | | 220 | |
| GGT | AGC | TCT | AAT | TCG | AGC | GGT | CAT | GGA | ATG | GAA | GGA | GAT | CTT | CCT | GCC | 843 |
| Gly | Ser | Ser | Asn | Ser | Ser | Gly | His | Gly | Met | Glu | Gly | Asp | Leu | Pro | Ala | |
| | | | | 225 | | | | | 230 | | | | | 235 | | |
| GCG | TGG | CGC | AAC | GCG | TTC | ACC | GCT | GCT | AAC | GCC | ACA | CCT | GAG | GGT | CGC | 891 |
| Ala | Trp | Arg | Asn | Ala | Phe | Thr | Ala | Ala | Asn | Ala | Thr | Pro | Glu | Gly | Arg | |
| | | | 240 | | | | | 245 | | | | | 250 | | | |
| GCA | CGC | ATG | GCA | CTA | GCC | TTT | GCG | CTC | GGT | CAG | TGG | TCT | CCG | TGG | TTG | 939 |
| Ala | Arg | Met | Ala | Leu | Ala | Phe | Ala | Leu | Gly | Gln | Trp | Ser | Pro | Trp | Leu | |
| | | 255 | | | | | 260 | | | | | 265 | | | | |
| GCC | GAC | AAC | ACG | CCC | CAA | CCT | GAT | CTC | GAT | GAT | CCT | GAG | GCC | ATC | GCG | 987 |
| Ala | Asp | Asn | Thr | Pro | Gln | Pro | Asp | Leu | Asp | Asp | Pro | Glu | Ala | Ile | Ala | |
| | 270 | | | | | 275 | | | | | 280 | | | | | |
| GAT | TCC | GTA | TAT | GAG | TCT | GCC | ATG | CGA | CTT | GCA | GGA | AGC | CCT | GGG | GGA | 1035 |
| Asp | Ser | Val | Tyr | Glu | Ser | Ala | Met | Arg | Leu | Ala | Gly | Ser | Pro | Gly | Gly | |
| 285 | | | | | 290 | | | | | 295 | | | | | 300 | |
| GAA | GCG | CGC | ATA | ATG | TTC | GAG | AAC | GCC | GCT | CGA | GGG | CAA | CAG | CTC | TCT | 1083 |
| Glu | Ala | Arg | Ile | Met | Phe | Glu | Asn | Ala | Ala | Arg | Gly | Gln | Gln | Leu | Ser | |
| | | | | 305 | | | | | 310 | | | | | 315 | | |
| TGG | AAC | GAC | GAC | ATC | GAC | TAT | GCG | GAT | TTC | TGG | GAG | AAC | TCA | AAC | CCA | 1131 |
| Trp | Asn | Asp | Asp | Ile | Asp | Tyr | Ala | Asp | Phe | Trp | Glu | Asn | Ser | Asn | Pro | |
| | | | 320 | | | | | 325 | | | | | 330 | | | |
| GCC | ATG | AAG | AGC | GCC | GTT | CAG | GAG | CTG | TAC | GAC | ACG | GCC | GGC | CTT | GAT | 1179 |
| Ala | Met | Lys | Ser | Ala | Val | Gln | Glu | Leu | Tyr | Asp | Thr | Ala | Gly | Leu | Asp | |
| | | 335 | | | | | 340 | | | | | 345 | | | | |

```
CTG CAG TCC GAT ATA GAA ACG GTA AAT TCC CAG CCA CGC ATA GAG GCA      1227
Leu Gln Ser Asp Ile Glu Thr Val Asn Ser Gln Pro Arg Ile Glu Ala
        350                 355                 360

TCG CAG TAT GCG CTC GAC TAC TGG AAC ACG CCA GGT CGC AAT GTC ATT      1275
Ser Gln Tyr Ala Leu Asp Tyr Trp Asn Thr Pro Gly Arg Asn Val Ile
365                     370                 375                 380

GGC GAC CCC GAA GTT CCT GTG CTG CGC CTG CAT ATG ATA GGC GAC TAC      1323
Gly Asp Pro Glu Val Pro Val Leu Arg Leu His Met Ile Gly Asp Tyr
                    385                 390                 395

CAA ATT CCC TAT AGT CTT GTA CAG GGC TAC AGC GAT CTT ATC TCA GAG      1371
Gln Ile Pro Tyr Ser Leu Val Gln Gly Tyr Ser Asp Leu Ile Ser Glu
        400                 405                 410

AAC AAC AAT GAT GAC TTG TAC AGA ACT GCT TTT GTG CAA TCC ACT GGA      1419
Asn Asn Asn Asp Asp Leu Tyr Arg Thr Ala Phe Val Gln Ser Thr Gly
            415                 420                 425

CAC TGC AAT TTC ACA GCT GCA GAA AGT TCC GCT GCG ATT GAG GTC ATG      1467
His Cys Asn Phe Thr Ala Ala Glu Ser Ser Ala Ala Ile Glu Val Met
        430                 435                 440

ATG CAA CGG CTT GAC ACG GGT GAG TGG CCG AGC ACC GAG CCG GAT GAT      1515
Met Gln Arg Leu Asp Thr Gly Glu Trp Pro Ser Thr Glu Pro Asp Asp
445                     450                 455                 460

CTG AAT GCA ATT GCC GAA GCC TCA AAC ACC GGA ACT GAA GCA CGT TTC      1563
Leu Asn Ala Ile Ala Glu Ala Ser Asn Thr Gly Thr Glu Ala Arg Phe
                    465                 470                 475

ATG GCC CTA GAT GGC TGG GAA ATA CCC GAG TAC AAT CGT ACT TGG AAG      1611
Met Ala Leu Asp Gly Trp Glu Ile Pro Glu Tyr Asn Arg Thr Trp Lys
        480                 485                 490

CCT GAA TAATCACCAT TCTGGAGGCT CACGTTCGCG AAGGGTTGCG GCGAAGAAAA       1667
Pro Glu
CATGCCGCC AACCTATCCT CCAAACAAGG GCCAGTTCAA CGACGAACAA GCCAGACCGG     1727
CGCAAGCCGC GCTAATCTAA TTCACCGCTC CAACCCGCGA TCTCGCGACC GCCCGCGCTG     1787
CATGTCGAGC TTCTGTTGCT GCGCCCGCTC AAGCGTATAA TCACGCCGGA TAATCGTTTC     1847
CCGCGCTTTG TTCGTGATCC TTGCAACGTC CTTGATGCGA TCGACGTTAC GGGCTGTCTC     1907
TGAAGGCTGT GAGCGTGTGC GATCAAGCGC CTGATCGATA TCGCGATGAT TGCTTGATCC     1967
GAACCGGATC TGCATAGCCC GGGCAATACG TTTGGCTTCA TCAAGCGCCT GTTTGCCATC     2027
AGCCGTCTTT TCGAGCTGAT CGACAAAGCC CGTCCGTGCC TTCGCATCCT TGATCTGATC     2087
GAGCTGCCTG AGCAGGGTTT CGCTGCGAGG TGAGAGGCCA GGAATCTCGA CGCGATCATT     2147
ATTGTCACGC CGCCATTGTT CGGCTTCCTT TTCCTCGGCA AAGCGCCGCG TCCAGGTCTT     2207
CCCCGCCGCG TCCAGATGCG AACTCATCGC CTCGGCCCGC TTGAGGGCAT TTTTTGCGCT     2267
CGGCATTGGC ACCGAACAGG CCGAACTTGC CGCGCAGCTG TTGATTTCTG CTGAGAAGTG     2327
ACCCGGTATT GGAGTGAACC CCTGGGACTG GACCAGCGGG GAAGAAAAGC TGATACGCTC     2387
TGTGGGCCTT GAATGGAGAA GGTCCATGTC ACCAAGAGGT CCCTACCGCC GTCACTCGAT     2447
GCAGTTCAAG CGTAAGCGCC AAGCCTGGCC CGTCTGGTGA TGGCTGCCTT TGAGCGCTAT     2507
CGACACCCCG GAGTTAGTGA TGGGTGTCAT GTTCTATGTC TGCGACTATG CCTGCAGATA     2567
GAAGTTTCCA GTTGATCGAG GCGGTTCCGG ATCGGATGGA GGGCGCTCCG GTTGCGCGGC     2627
GACGCCGGTG GTCGGACGCG TTCAAGGCCG AGATGGTAGC GCGCAGCTTC GAACCTGGAA     2687
CGAATGTGTC GGCACTGGCG CGCGAGATCG GCATCCAGTC CTCGCAGTTG TTCGGCTGGC     2747
GCGCCGAGGC CCTCAAGCGC GGAGAGGTGG AAAGGCGCGA TGTTGATATC GTTGCAACGC     2807
AAGCCTCTCG CTTGGTGAGC GGGACGGTCG AGATCGCGGT CAACGACACG GTGATCCGGG     2867
TCGGCATTGA TATCGGGGAA GACCATTTGC GGCGCGTGAT CCGCGCTGTG CGGTCGGCAT     2927
```

```
GATCCCTGCG GGTGTGAAGG TCTATCTGGC CAGCCAGCCG GTAGACTTCA GGAAAGGTCC         2987

AGACGGCCTT GTTGGCCTGG TGCGCGATGC TGGAGCGGAT CC                           3029
```

( 2 ) INFORMATION FOR SEQ ID NO:7:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
GGATCCTTAG GAATCTAAAC ATTCTGGTTG ACACTCCACA TTTTGAATGT CAGCATTTCG          60

GCCATGGCTG CTATGCAGCC TGTTATTGCA TTTGAAATGG AATAGATCAG CAAACTTATC         120

GGGAGGATGA GTATT                                                         135
```

( 2 ) INFORMATION FOR SEQ ID NO:8:

( i ) SEQUENCE CHARACTERISTICS:
        ( A ) LENGTH: 126 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..126

( x i ) SEQUENCE DESCRIPTION: SEQ ID NO:8:

```
ATG ATA ATC AAG GGT AGT GTA CCG GGT AAA GCC GGA GGA AAA CCT CGA           48
Met Ile Ile Lys Gly Ser Val Pro Gly Lys Ala Gly Gly Lys Pro Arg
 1               5                  10                  15

GCG ACC ATC TTT CAT AGT TCT ATT GCA ACG CTA CTT TTA ACC ACA GTC           96
Ala Thr Ile Phe His Ser Ser Ile Ala Thr Leu Leu Leu Thr Thr Val
             20                  25                  30

TCA CTG TCA GGA GTA GCG CCA GCA TTT GCA                                  126
Ser Leu Ser Gly Val Ala Pro Ala Phe Ala
         35                  40
```

( 2 ) INFORMATION FOR SEQ ID NO:9:

( i ) SEQUENCE CHARACTERISTICS:
        ( A ) LENGTH: 42 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Ile Ile Lys Gly Ser Val Pro Gly Lys Ala Gly Gly Lys Pro Arg
 1               5                  10                  15

Ala Thr Ile Phe His Ser Ser Ile Ala Thr Leu Leu Leu Thr Thr Val
             20                  25                  30

Ser Leu Ser Gly Val Ala Pro Ala Phe Ala
         35                  40
```

( 2 ) INFORMATION FOR SEQ ID NO:10:

( i ) SEQUENCE CHARACTERISTICS:
        ( A ) LENGTH: 1409 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:10:

```
TCACCATTCT GGAGGCTCAC GTTCGCGAAG GGTTGCGGCG AAGAAAACAT GCGCCGCAAC        60
CTATCCTCCA AACAAGGGCC AGTTCAACGA CGAACAAGCC AGACCGGCGC AAGCCGCGCT       120
AATCTAATTC ACCGCTCCAA CCCGCGATCT CGCGACCGCC CGCGCTGCAT GTCGAGCTTC       180
TGTTGCTGCG CCCGCTCAAG CGTATAATCA CGCCGGATAA TCGTTTCCCG CGCTTTGTTC       240
GTGATCCTTG CAACGTCCTT GATGCGATCG ACGTTACGGG CTGTCTCTGA AGGCTGTGAG       300
CGTGTGCGAT CAAGCGCCTG ATCGATATCG CGATGATTGC TTGATCCGAA CCGGATCTGC       360
ATAGCCCGGG CAATACGTTT GGCTTCATCA AGCGCCTGTT TGCCATCAGC CGTCTTTTCG       420
AGCTGATCGA CAAAGCCCGT CCGTGCCTTC GCATCCTTGA TCTGATCGAG CTGCCTGAGC       480
AGGGTTTCGC TGCGAGGTGA GAGGCCAGGA ATCTCGACGC GATCATTATT GTCACGCCGC       540
CATTGTTCGG CTTCCTTTTC CTCGGCAAAG CGCCGCGTCC AGGTCTTCCC CGCCGCGTCC       600
AGATGCGAAC TCATCGCCTC GGCCCGCTTG AGGGCATTTT TTGCGCTCGG CATTGGCACC       660
GAACAGGCCG AACTTGCCGC GCAGCTGTTG ATTTCTGCTG AGAAGTGACC CGGTATTGGA       720
GTGAACCCCT GGGACTGGAC CAGCGGGGAA GAAAAGCTGA TACGCTCTGT GGGCCTTGAA       780
TGGAGAAGGT CCATGTCACC AAGAGGTCCC TACCGCCGTC ACTCGATGCA GTTCAAGCGT       840
AAGCGCCAAG CCTGGCCCGT CTGGTGATGG CTGCCTTTGA GCGCTATCGA CACCCCGGAG       900
TTAGTGATGG GTGTCATGTT CTATGTCTGC GACTATGCCT GCAGATAGAA GTTTCCAGTT       960
GATCGAGGCG GTTCCGGATC GGATGGAGGG CGCTCCGGTT GCGCGGCGAC GCCGGTGGTC      1020
GGACGCGTTC AAGGCCGAGA TGGTAGCGCG CAGCTTCGAA CCTGGAACGA ATGTGTCGGC      1080
ACTGGCGCGC GAGATCGGCA TCCAGTCCTC GCAGTTGTTC GGCTGGCGCG CCGAGGCCCT      1140
CAAGCGCGGA GAGGTGGAAA GGCGCGATGT TGATATCGTT GCAACGCAAG CCTCTCGCTT      1200
GGTGAGCGGG ACGGTCGAGA TCGCGGTCAA CGACACGGTG ATCCGGGTCG GCATTGATAT      1260
CGGGGAAGAC CATTTGCGGC GCGTGATCCG CGCTGTGCGG TCGGCATGAT CCCTGCGGGT      1320
GTGAAGGTCT ATCTGGCCAG CCAGCCGGTA GACTTCAGGA AAGGTCCAGA CGGCCTTGTT      1380
GGCCTGGTGC GCGATGCTGG AGCGGATCC                                       1409
```

(2) INFORMATION FOR SEQ ID NO:11:

(i) SEQUENCE CHARACTERISTICS:
(A) LENGTH: 1362 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..1359

(xi) SEQUENCE DESCRIPTION: SEQ ID NO:11:

```
ATG CAG GCG CCG TCT GTG CAC CAA CAC GTC GCC TTC ACT GAG GAA ATT        48
Met Gln Ala Pro Ser Val His Gln His Val Ala Phe Thr Glu Glu Ile
  1               5                  10                  15

GGA GAC CTT CCC GAC GGC TCA AGT TAC ATG ATC CGT GTG CCG GAG AAC        96
Gly Asp Leu Pro Asp Gly Ser Ser Tyr Met Ile Arg Val Pro Glu Asn
             20                  25                  30
```

-continued

| | | | | | | | | | | | | | | | | |
|---|---|---|---|---|---|---|---|---|---|---|---|---|---|---|---|---|
| TGG | AAC | GGC | GTG | TTA | ATT | CGC | GAC | CTA | GAC | CTT | GTC | AGC | GGC | ACC | AGC | 144 |
| Trp | Asn | Gly | Val | Leu | Ile | Arg | Asp | Leu | Asp | Leu | Val | Ser | Gly | Thr | Ser | |
| | | 35 | | | | 40 | | | | | 45 | | | | | |
| AAT | TCT | AAC | GCC | GCA | AGG | TAC | GAA | ACC | ATG | CTG | AAA | GAA | GGT | TTT | GCC | 192 |
| Asn | Ser | Asn | Ala | Ala | Arg | Tyr | Glu | Thr | Met | Leu | Lys | Glu | Gly | Phe | Ala | |
| | 50 | | | | | 55 | | | | | 60 | | | | | |
| GTT | GCT | GGC | ACG | GCG | AGG | CAT | CCC | CTT | CGG | CAA | TGG | CAA | TAT | GAC | CCC | 240 |
| Val | Ala | Gly | Thr | Ala | Arg | His | Pro | Leu | Arg | Gln | Trp | Gln | Tyr | Asp | Pro | |
| 65 | | | | | 70 | | | | | 75 | | | | | 80 | |
| GCT | CAC | GAG | ATT | GAA | AAC | CTC | AAT | CAC | GTG | CTG | GAC | ACA | TTC | GAG | GAA | 288 |
| Ala | His | Glu | Ile | Glu | Asn | Leu | Asn | His | Val | Leu | Asp | Thr | Phe | Glu | Glu | |
| | | | | 85 | | | | | 90 | | | | | 95 | | |
| AAT | TAC | GGT | TCA | CCT | GAA | AGA | GTT | ATC | CAG | TAC | GGT | TGC | TCG | GGT | GGG | 336 |
| Asn | Tyr | Gly | Ser | Pro | Glu | Arg | Val | Ile | Gln | Tyr | Gly | Cys | Ser | Gly | Gly | |
| | | | 100 | | | | | 105 | | | | | 110 | | | |
| GCA | CAC | GTG | TCA | CTA | GCC | GTG | GCA | GAG | GAC | TTC | TCG | GAC | CGC | GTA | GAT | 384 |
| Ala | His | Val | Ser | Leu | Ala | Val | Ala | Glu | Asp | Phe | Ser | Asp | Arg | Val | Asp | |
| | | 115 | | | | | 120 | | | | | 125 | | | | |
| GGC | TCA | GTT | GCT | CTA | GCT | GCT | CAT | ACT | CCT | GTC | TGG | ATA | ATG | AAT | TCT | 432 |
| Gly | Ser | Val | Ala | Leu | Ala | Ala | His | Thr | Pro | Val | Trp | Ile | Met | Asn | Ser | |
| | 130 | | | | | 135 | | | | | 140 | | | | | |
| TTC | TTG | GAC | GGA | TGG | TTT | TCG | CTG | CAG | TCT | CTG | ATC | GGC | GAG | TAC | TAT | 480 |
| Phe | Leu | Asp | Gly | Trp | Phe | Ser | Leu | Gln | Ser | Leu | Ile | Gly | Glu | Tyr | Tyr | |
| 145 | | | | | 150 | | | | | 155 | | | | | 160 | |
| GTA | GAA | GCT | GGT | CAC | GGC | CCA | CTT | TCG | GAT | CTC | GCT | ATT | ACG | AAA | CTG | 528 |
| Val | Glu | Ala | Gly | His | Gly | Pro | Leu | Ser | Asp | Leu | Ala | Ile | Thr | Lys | Leu | |
| | | | | 165 | | | | | 170 | | | | | 175 | | |
| CCC | AAT | GAT | GGT | AGC | TCT | AAT | TCG | AGC | GGT | CAT | GGA | ATG | GAA | GGA | GAT | 576 |
| Pro | Asn | Asp | Gly | Ser | Ser | Asn | Ser | Ser | Gly | His | Gly | Met | Glu | Gly | Asp | |
| | | | 180 | | | | | 185 | | | | | 190 | | | |
| CTT | CCT | GCC | GCG | TGG | CGC | AAC | GCG | TTC | ACC | GCT | GCT | AAC | GCC | ACA | CCT | 624 |
| Leu | Pro | Ala | Ala | Trp | Arg | Asn | Ala | Phe | Thr | Ala | Ala | Asn | Ala | Thr | Pro | |
| | | 195 | | | | | 200 | | | | | 205 | | | | |
| GAG | GGT | CGC | GCA | CGC | ATG | GCA | CTA | GCC | TTT | GCG | CTC | GGT | CAG | TGG | TCT | 672 |
| Glu | Gly | Arg | Ala | Arg | Met | Ala | Leu | Ala | Phe | Ala | Leu | Gly | Gln | Trp | Ser | |
| | 210 | | | | | 215 | | | | | 220 | | | | | |
| CCG | TGG | TTG | GCC | GAC | AAC | ACG | CCC | CAA | CCT | GAT | CTC | GAT | GAT | CCT | GAG | 720 |
| Pro | Trp | Leu | Ala | Asp | Asn | Thr | Pro | Gln | Pro | Asp | Leu | Asp | Asp | Pro | Glu | |
| 225 | | | | | 230 | | | | | 235 | | | | | 240 | |
| GCC | ATC | GCG | GAT | TCC | GTA | TAT | GAG | TCT | GCC | ATG | CGA | CTT | GCA | GGA | AGC | 768 |
| Ala | Ile | Ala | Asp | Ser | Val | Tyr | Glu | Ser | Ala | Met | Arg | Leu | Ala | Gly | Ser | |
| | | | | 245 | | | | | 250 | | | | | 255 | | |
| CCT | GGG | GGA | GAA | GCG | CGC | ATA | ATG | TTC | GAG | AAC | GCC | GCT | CGA | GGG | CAA | 816 |
| Pro | Gly | Gly | Glu | Ala | Arg | Ile | Met | Phe | Glu | Asn | Ala | Ala | Arg | Gly | Gln | |
| | | | 260 | | | | | 265 | | | | | 270 | | | |
| CAG | CTC | TCT | TGG | AAC | GAC | GAC | ATC | GAC | TAT | GCG | GAT | TTC | TGG | GAG | AAC | 864 |
| Gln | Leu | Ser | Trp | Asn | Asp | Asp | Ile | Asp | Tyr | Ala | Asp | Phe | Trp | Glu | Asn | |
| | | 275 | | | | | 280 | | | | | 285 | | | | |
| TCA | AAC | CCA | GCC | ATG | AAG | AGC | GCC | GTT | CAG | GAG | CTG | TAC | GAC | ACG | GCC | 912 |
| Ser | Asn | Pro | Ala | Met | Lys | Ser | Ala | Val | Gln | Glu | Leu | Tyr | Asp | Thr | Ala | |
| | 290 | | | | | 295 | | | | | 300 | | | | | |
| GGC | CTT | GAT | CTG | CAG | TCC | GAT | ATA | GAA | ACG | GTA | AAT | TCC | CAG | CCA | CGC | 960 |
| Gly | Leu | Asp | Leu | Gln | Ser | Asp | Ile | Glu | Thr | Val | Asn | Ser | Gln | Pro | Arg | |
| 305 | | | | | 310 | | | | | 315 | | | | | 320 | |
| ATA | GAG | GCA | TCG | CAG | TAT | GCG | CTC | GAC | TAC | TGG | AAC | ACG | CCA | GGT | CGC | 1008 |
| Ile | Glu | Ala | Ser | Gln | Tyr | Ala | Leu | Asp | Tyr | Trp | Asn | Thr | Pro | Gly | Arg | |
| | | | | 325 | | | | | 330 | | | | | 335 | | |
| AAT | GTC | ATT | GGC | GAC | CCC | GAA | GTT | CCT | GTG | CTG | CGC | CTG | CAT | ATG | ATA | 1056 |
| Asn | Val | Ile | Gly | Asp | Pro | Glu | Val | Pro | Val | Leu | Arg | Leu | His | Met | Ile | |
| | | | 340 | | | | | 345 | | | | | 350 | | | |

| | | | | | | | | | | | | | | | | |
|---|---|---|---|---|---|---|---|---|---|---|---|---|---|---|---|---|
| GGC | GAC | TAC | CAA | ATT | CCC | TAT | AGT | CTT | GTA | CAG | GGC | TAC | AGC | GAT | CTT | 1104 |
| Gly | Asp | Tyr | Gln | Ile | Pro | Tyr | Ser | Leu | Val | Gln | Gly | Tyr | Ser | Asp | Leu | |
| | | 355 | | | | 360 | | | | | | 365 | | | | |
| ATC | TCA | GAG | AAC | AAC | AAT | GAT | GAC | TTG | TAC | AGA | ACT | GCT | TTT | GTG | CAA | 1152 |
| Ile | Ser | Glu | Asn | Asn | Asn | Asp | Asp | Leu | Tyr | Arg | Thr | Ala | Phe | Val | Gln | |
| 370 | | | | | 375 | | | | | | 380 | | | | | |
| TCC | ACT | GGA | CAC | TGC | AAT | TTC | ACA | GCT | GCA | GAA | AGT | TCC | GCT | GCG | ATT | 1200 |
| Ser | Thr | Gly | His | Cys | Asn | Phe | Thr | Ala | Ala | Glu | Ser | Ser | Ala | Ala | Ile | |
| 385 | | | | | 390 | | | | | 395 | | | | | 400 | |
| GAG | GTC | ATG | ATG | CAA | CGG | CTT | GAC | ACG | GGT | GAG | TGG | CCG | AGC | ACC | GAG | 1248 |
| Glu | Val | Met | Met | Gln | Arg | Leu | Asp | Thr | Gly | Glu | Trp | Pro | Ser | Thr | Glu | |
| | | | | 405 | | | | | 410 | | | | | 415 | | |
| CCG | GAT | GAT | CTG | AAT | GCA | ATT | GCC | GAA | GCC | TCA | AAC | ACC | GGA | ACT | GAA | 1296 |
| Pro | Asp | Asp | Leu | Asn | Ala | Ile | Ala | Glu | Ala | Ser | Asn | Thr | Gly | Thr | Glu | |
| | | | 420 | | | | | 425 | | | | | 430 | | | |
| GCA | CGT | TTC | ATG | GCC | CTA | GAT | GGC | TGG | GAA | ATA | CCC | GAG | TAC | AAT | CGT | 1344 |
| Ala | Arg | Phe | Met | Ala | Leu | Asp | Gly | Trp | Glu | Ile | Pro | Glu | Tyr | Asn | Arg | |
| | | 435 | | | | | 440 | | | | | 445 | | | | |
| ACT | TGG | AAG | CCT | GAA | TAA | | | | | | | | | | | 1362 |
| Thr | Trp | Lys | Pro | Glu | | | | | | | | | | | | |
| | | 450 | | | | | | | | | | | | | | |

( 2 ) INFORMATION FOR SEQ ID NO:12:

( i ) SEQUENCE CHARACTERISTICS:
        ( A ) LENGTH: 453 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Gln | Ala | Pro | Ser | Val | His | Gln | His | Val | Ala | Phe | Thr | Glu | Glu | Ile |
| 1 | | | | 5 | | | | | 10 | | | | | 15 | |
| Gly | Asp | Leu | Pro | Asp | Gly | Ser | Ser | Tyr | Met | Ile | Arg | Val | Pro | Glu | Asn |
| | | | 20 | | | | | 25 | | | | | 30 | | |
| Trp | Asn | Gly | Val | Leu | Ile | Arg | Asp | Leu | Asp | Leu | Val | Ser | Gly | Thr | Ser |
| | | 35 | | | | | 40 | | | | | 45 | | | |
| Asn | Ser | Asn | Ala | Ala | Arg | Tyr | Glu | Thr | Met | Leu | Lys | Glu | Gly | Phe | Ala |
| | 50 | | | | | 55 | | | | | 60 | | | | |
| Val | Ala | Gly | Thr | Ala | Arg | His | Pro | Leu | Arg | Gln | Trp | Gln | Tyr | Asp | Pro |
| 65 | | | | | 70 | | | | | 75 | | | | | 80 |
| Ala | His | Glu | Ile | Glu | Asn | Leu | Asn | His | Val | Leu | Asp | Thr | Phe | Glu | Glu |
| | | | | 85 | | | | | 90 | | | | | 95 | |
| Asn | Tyr | Gly | Ser | Pro | Glu | Arg | Val | Ile | Gln | Tyr | Gly | Cys | Ser | Gly | Gly |
| | | | 100 | | | | | 105 | | | | | 110 | | |
| Ala | His | Val | Ser | Leu | Ala | Val | Ala | Glu | Asp | Phe | Ser | Asp | Arg | Val | Asp |
| | | 115 | | | | | 120 | | | | | 125 | | | |
| Gly | Ser | Val | Ala | Leu | Ala | Ala | His | Thr | Pro | Val | Trp | Ile | Met | Asn | Ser |
| | 130 | | | | | 135 | | | | | 140 | | | | |
| Phe | Leu | Asp | Gly | Trp | Phe | Ser | Leu | Gln | Ser | Leu | Ile | Gly | Glu | Tyr | Tyr |
| 145 | | | | | 150 | | | | | 155 | | | | | 160 |
| Val | Glu | Ala | Gly | His | Gly | Pro | Leu | Ser | Asp | Leu | Ala | Ile | Thr | Lys | Leu |
| | | | | 165 | | | | | 170 | | | | | 175 | |
| Pro | Asn | Asp | Gly | Ser | Ser | Asn | Ser | Ser | Gly | His | Gly | Met | Glu | Gly | Asp |
| | | | 180 | | | | | 185 | | | | | 190 | | |
| Leu | Pro | Ala | Ala | Trp | Arg | Asn | Ala | Phe | Thr | Ala | Ala | Asn | Ala | Thr | Pro |
| | | 195 | | | | | 200 | | | | | 205 | | | |
| Glu | Gly | Arg | Ala | Arg | Met | Ala | Leu | Ala | Phe | Ala | Leu | Gly | Gln | Trp | Ser |

```
              210                    215                     220
Pro  Trp  Leu  Ala  Asp  Asn  Thr  Pro  Gln  Pro  Asp  Leu  Asp  Asp  Pro  Glu
225                      230                 235                          240

Ala  Ile  Ala  Asp  Ser  Val  Tyr  Glu  Ser  Ala  Met  Arg  Leu  Ala  Gly  Ser
                    245                      250                     255

Pro  Gly  Gly  Glu  Ala  Arg  Ile  Met  Phe  Glu  Asn  Ala  Ala  Arg  Gly  Gln
               260                      265                          270

Gln  Leu  Ser  Trp  Asn  Asp  Asp  Ile  Asp  Tyr  Ala  Asp  Phe  Trp  Glu  Asn
          275                      280                     285

Ser  Asn  Pro  Ala  Met  Lys  Ser  Ala  Val  Gln  Glu  Leu  Tyr  Asp  Thr  Ala
     290                      295                      300

Gly  Leu  Asp  Leu  Gln  Ser  Asp  Ile  Glu  Thr  Val  Asn  Ser  Gln  Pro  Arg
305                      310                     315                          320

Ile  Glu  Ala  Ser  Gln  Tyr  Ala  Leu  Asp  Tyr  Trp  Asn  Thr  Pro  Gly  Arg
                    325                      330                     335

Asn  Val  Ile  Gly  Asp  Pro  Glu  Val  Pro  Val  Leu  Arg  Leu  His  Met  Ile
               340                      345                     350

Gly  Asp  Tyr  Gln  Ile  Pro  Tyr  Ser  Leu  Val  Gln  Gly  Tyr  Ser  Asp  Leu
          355                      360                     365

Ile  Ser  Glu  Asn  Asn  Asn  Asp  Leu  Tyr  Arg  Thr  Ala  Phe  Val  Gln
     370                      375                     380

Ser  Thr  Gly  His  Cys  Asn  Phe  Thr  Ala  Ala  Glu  Ser  Ser  Ala  Ala  Ile
385                      390                     395                          400

Glu  Val  Met  Met  Gln  Arg  Leu  Asp  Thr  Gly  Glu  Trp  Pro  Ser  Thr  Glu
                    405                      410                     415

Pro  Asp  Asp  Leu  Asn  Ala  Ile  Ala  Glu  Ala  Ser  Asn  Thr  Gly  Thr  Glu
               420                      425                     430

Ala  Arg  Phe  Met  Ala  Leu  Asp  Gly  Trp  Glu  Ile  Pro  Glu  Tyr  Asn  Arg
          435                      440                     445

Thr  Trp  Lys  Pro  Glu
450
```

( 2 ) INFORMATION FOR SEQ ID NO:13:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2..78

( x i ) SEQUENCE DESCRIPTION: SEQ ID NO:13:

```
T CGA GCG ACC ATC TTT CAT AGT TCT ATT GCA ACG CTA CTT TTA ACC       46
  Arg Ala Thr Ile Phe His Ser Ser Ile Ala Thr Leu Leu Leu Thr
  1               5                   10                  15

ACA GTC TCA CTG TCA GGA GTA GCG CCA GCA TTT GC                      81
Thr Val Ser Leu Ser Gly Val Ala Pro Ala Phe
                20              25              30
```

( 2 ) INFORMATION FOR SEQ ID NO:14:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
TAGCAAATGC  TGGCGCTACT  CCTGACAGTG  AGACTGTGGT  TAAAAGTAGC  GTTGCAATAG      60

AACTATGAAA  GATGGTCGC                                                      79
```